(12) United States Patent
Kinkema et al.

(10) Patent No.: US 9,441,234 B2
(45) Date of Patent: Sep. 13, 2016

(54) COMPOSITIONS AND METHODS FOR INCREASED EXPRESSION IN SUGAR CANE

(71) Applicants: Mark D. Kinkema, St. Lucia (AU); Stacy Miles, Durham, NC (US)

(72) Inventors: Mark D. Kinkema, St. Lucia (AU); Stacy Miles, Durham, NC (US)

(73) Assignees: SYNGENTA PARTICIPATIONS AG, Basel (CH); QUEENSLAND UNIVERSITY OF TECHNOLOGY, Brisbane (AU)

(*) Notice: Subject to any disclaimer, the term of this patent is extended or adjusted under 35 U.S.C. 154(b) by 207 days.

(21) Appl. No.: 14/364,184

(22) PCT Filed: Dec. 7, 2012

(86) PCT No.: PCT/US2012/068409
§ 371 (c)(1),
(2) Date: Jun. 10, 2014

(87) PCT Pub. No.: WO2013/090137
PCT Pub. Date: Jun. 20, 2013

(65) Prior Publication Data
US 2014/0366220 A1 Dec. 11, 2014

Related U.S. Application Data

(60) Provisional application No. 61/576,112, filed on Dec. 15, 2011.

(51) Int. Cl.
C12N 15/82 (2006.01)

(52) U.S. Cl.
CPC ....... *C12N 15/8245* (2013.01); *C12N 15/8216* (2013.01)

(58) Field of Classification Search
None
See application file for complete search history.

(56) References Cited

U.S. PATENT DOCUMENTS

| 7,166,770 B2 | 1/2007 | Hohn et al. | |
| 7,816,506 B2 * | 10/2010 | Mirkov | C07K 14/415 536/23.4 |
| 2010/0009851 A1 | 1/2010 | Lee et al. | |

FOREIGN PATENT DOCUMENTS

| CN | 1884548 | 12/2006 |
| CN | 101768604 | 7/2010 |
| WO | WO 2011/011685 A1 | 1/2010 |
| WO | WO 2010/151634 A1 | 12/2010 |
| WO | WO 2011/084370 A1 | 7/2011 |

OTHER PUBLICATIONS

International Search Report and Written Opinion Corresponding to International Application No. PCT/US2012/068409; Date of Mailing: Feb. 27, 2013; 13 Pages.

International Preliminary Report on Patentability Corresponding to International Application No. PCT/US2012/068409; Date of Mailing: Jun. 26, 2014; 8 Pages.

Assaad et al. (1993) Epigenetic repeat-induced gene silencing (RIGS) in *Arabidopsis. Plant Mol. Biol.*, 22, 1067-1085.

Basnayake et al. (2012) Field performance of transgenic sugarcane expressing isomaltulose synthase. *Plant Biotech. J.*, 10(2):217-2125.

Beyene et al. (2011) Unprecedented enhancement of transient gene expression from minimal cassettes using a double terminator. *Plant Cell Rep.*, 30, 13-25.

Birch et al. (2010) Highly efficient, 5' sequence-specific transgene silencing in a complex polyploidy. *Tropical Plant Biol.*, 3, 88-97.

Birch, R.G., Bower, R., Elliott, A.R., Potier, B.A.M., Franks, T., and Cordeiro, G. (1996) Expression of foreign genes in sugarcane. In: Cock JH, Brekelbaum T (eds) Proc. Int. Soc. Sugarcane Technol. XXII Congress. Tecnicana, Cali, 368-373.

Braithwaite et al. (2004) A variable region of the sugarcane baciliform virus (SCBV) genome can be used to generate promoters for transgene expression in sugarcane. *Plant Cell Rep.*, 23, 319-326.

Callis et al. (1987) Introns increase gene expression in cultured maize cells. *Genes Dev.*, 1, 1183-1200.

Casu et al. (2003) Identification of a novel sugar transporter homologue strongly expressed in maturing stem vascular tissues of sugarcane by expressed sequence tag and microarray analysis. *Plant Mol. Biol.*, 52, 371-386.

Casu et al. (2004) Identification of differentially expressed transcripts from maturing stem of sugarcane by in silico analysis of stem expressed sequence tags and gene expression profiling. *Plant Mol. Biol.*, 54, 503-517.

Casu et al. (2007) Identification of transcripts associated with cell wall metabolism and development in the stem of sugarcane by Affymetrix GeneChip Sugarcane Genome Array expression profiling. *Funct. Integr. Genomics*, 7, 153-167.

Christie et al. (2011) Intron splicing suppresses RNA silencing in *Arabidopsis. Plant J.*, 68:159-167.

Christy et al. (2009) Engineering sugarcane cultivars with bovine pancreatic trypsin inhibitor (aprotinin) gene for protection against top borer (Scirpophaga excerptalis Walker). *Plant Cell Rep.*, 28, 175-184.

David-Assael et al. (2006) AtMHX is an auxin and ABA-regulated transporter whose expression pattern suggests a role in metal homeostasis in tissues with photosynthetic potential. *Functional Plant Biology*, 33, 661-672.

(Continued)

*Primary Examiner* — Elizabeth McElwain
(74) *Attorney, Agent, or Firm* — Myers Bigel & Sibley, P.A.

(57) ABSTRACT

A sugar cane plant cell comprising a recombinant nucleic acid molecule is provided, the recombinant nucleic acid molecule comprising a nucleotide sequence of interest, a promoter and the nucleotide sequence of SEQ ID NO:1, wherein the promoter is downstream of and in operative association with the nucleotide sequence of SEQ ID NO:1 and upstream of and in operative association with the nucleotide sequence of interest, and the nucleotide sequence of interest is expressed at a level at least about 6 times greater than the level of expression of said nucleotide sequence of interest in a control. Additionally, a method of increasing the expression of a nucleotide sequence of interest in a sugar cane plant cell using the recombinant nucleic acid molecule of the invention is provided.

12 Claims, 5 Drawing Sheets

(56) References Cited

OTHER PUBLICATIONS

Dugdale et al. (1998) Promoter activity associated with the intergenic regions of banana bunchy top virus DNA-1 to -6 in transgenic tobacco and banana cells. *J. Gen. Virol.*, 79, 2301-2311.

Dugdale et al. (2001) Intron-mediated enhancement of the banana bunchy top virus DNA-6 promoter in banana (*Musa* spp.) embryogenic cells and plants. *Plant Cell Rep.*, 20, 220-226.

Estruch et al. (1997) Transgenic plants: An emerging approach to pest control. *Nat. Biotech.* 15, 137-141.

Fu et al. (1995) A potato Sus3 sucrose synthase gene contains a context-dependent 3' element and a leader intron with both positive and negative tissue-specific effects. *Plant Cell*, 7, 1395-1403.

Gallie et al. (1987) a comparison of eukaryotic viral 5'-leader seqeunces as enhancers of mRNA expression in vivo. *Nucl. Acids Res.*, 15, 8693-8711.

Gehrig et al. (2009) Automated high-throughput mapping of promoter-enhancer interactions in zebrafish embryos. *Nat. Methods*, 6, 911-916.

Grof, C.P.L., Glassop, D., Quick, W.P., Sonnewald, U., and Campbell, J.A. (1996) Molecular manipulation of sucrose phosphate synthase in sugarcane. In J.R. Wilson et al. (ed) Sugarcane: Research towards efficient and sustainable production. CSIRO Division of Tropical Crops and Pastures, Brisbane, Australia. p. 124-126.

Hansom, S., Bower, R., Zhang, L., Potier, B., Elliott, A., Basnayake, S., Cordeiro, G., Hograth D.M., Cox, M., Berding, N., and Birch, R.G. (1999) Regulation of transgene expression in sugarcane. In: Singh V (ed) Proc. Int. Soc. Sugarcane Technol. XXIII congress. STAI, New Delhi, 278-290.

Harrison et al. (2011) Accumulation of recombinant cellobiohydrolase and endoglucananse in the leaves of mature transgenic sugar cane. *Plant Biotech. J.*, 9, 884-896.

He et al. (2009) Identification of a rice actin2 gene regulatory region for high-level expression of transgenes in monocots. *Plant Biotechnol J.*, 7, 227-239.

Hir et al. (2003) How introns influence and enhance eukaryotic gene expression. *Trends Biochem. Sci.*, 28, 215-220.

Jain et al. (2007) Prospecting the utility of a PMI/mannose selection system for the recovery of transgenic sugarcane (*Saccharum* spp. hybrid) plants. *Plant Cell Rep.*, 26, 581-590.

Jeon et al. (2000) Tissue-preferential expression of a rice α-tubulin gene, OsTubA1, mediated by the first intron. *Plant Physiol.*, 123, 1005-1014.

Mudge et al. (2009) Efficient silencing of reporter transgenes coupled to known functional promoters in sugarcane, a highly polyploid crop species. *Planta*, 229, 549-558.

Perlak et al. (1991) Modification of the coding sequence enhances plant expression of insect control protein genes. *Proc. Natl. Acad. Sci. USA.*, 88, 3324-3328.

Schenk et al. (1999) A promoter from sugarcane bacilliform badnavirus drives transgene expression in banana and other monocot and dicot plants. *Plant Mol. Biol.*, 39, 1221-1230.

Schubert et al. (2004) Silencing in Arabiodpsis T-DNA transformants: The predominant role of a gene-specific RNA sensing mechanism versus position effects. *Plant Cell*, 16, 2561-2572.

Singer et al. (2010) Both the constitutive Cauliflower Mosaic Virus 35S and tissue-specific AGAMOUS enhancers activate transcription autonomously in *Arabidopsis thaliana*. *Plant Mol. Biol.*, 74, 293-305.

Sivamani et al. (2006) Expression enhancement of a rice polyubiquitin gene promoter. *Plant Mol. Biol.*, 60, 225-239.

Wang et al. (2002) Regulation of the cell expansion gene RHD3 during *Arabiodpsis* development. *Plant Physiol.*, 129, 638-649.

Wu et al. (2007) Doubled sugar content in sugarcane plants modified to produce a sucrose isomer. *Plant Biotech. J.* 5, 109-117.

\* cited by examiner

```
                        SEQUENCE LISTING

<160> NUMBER OF SEQ ID NOS: 2

<210> SEQ ID NO 1
<211> LENGTH: 493
<212> TYPE: DNA
<213> ORGANISM: Artificial
<220> FEATURE:
<223> OTHER INFORMATION: Dual figwort mosaic virus/cauliflower mosaic
      virus transcription enhancer sequence

<400> SEQUENCE: 1
agctgcttgt ggggaccaga caaaaaagga atggtgcaga attgttaggc gcacctacca      60
aaagcatctt tgcctttatt gcaaagataa agcagattcc tctagtacaa gtggggaaca    120
aaataacgtg gaaagagct gtcctgacag cccactcact aatgcgtatg acgaacgcag     180
tgacgaccac aaaactcgag acttttcaac aaagggtaat atccggaaac ctcctcggat    240
tccattgccc agctatctgt cactttattg tgaagatagt ggaaaaggaa ggtggctcct    300
acaaatgcca tcattgcgat aaaggaaagg ctatcgttga agatgcctct gccgacagtg    360
gtcccaaaga tggaccccca cccacgagga gcatcgtgga aaaagaagac gttccaacca    420
cgtcttcaaa gcaagtggat tgatgtgata tctccactga cgtaagggat gacgaacaat    480
cccactatcc ttc                                                       493

<210> SEQ ID NO 2
<211> LENGTH: 68
<212> TYPE: DNA
<213> ORGANISM: Tobacco mosaic virus

<400> SEQUENCE: 2
gtatttttac aacaattacc aacaacaaca aacaacaaac aacattacaa ttactattta     60
caattaca                                                              68
```

COMPOSITIONS AND METHODS FOR INCREASED EXPRESSION IN SUGAR CANE

STATEMENT OF PRIORITY

This application is a 35 U.S.C. §371 national phase application of International Application Serial No. PCT/US2012/068409, filed Dec. 7, 2012, which claims the benefit, under 35 U.S.C. §119 (e), of U.S. Provisional Application No. 61/576,112; filed Dec. 15, 2011, the entire contents of which are incorporated by reference herein.

STATEMENT REGARDING ELECTRONIC FILING OF A SEQUENCE LISTING

A Sequence Listing in ASCII text format, submitted under 37 C.F.R. §1.821, entitled 9207-10_ST25.txt, 49,289 bytes in size, generated on Dec. 5, 2012 and filed via EFS-Web, is provided in lieu of a paper copy. This Sequence Listing is hereby incorporated herein by reference into the specification for its disclosures.

FIELD OF THE INVENTION

The present invention relates to compositions and methods for enhancing expression in sugar cane plants.

BACKGROUND

Sugar cane is one of the most important crops worldwide. It is the primary source of sugar for foods and beverages and for the production of biofuel. The difficulties and limitations associated with sugar cane breeding and the broad potential of genetic engineering make biotechnology an attractive approach for the improvement of priority traits in sugar cane such as increased sugar content and abiotic and biotic stress tolerance (Lakshmanan et al. *In vitro Cell. Dev. Biol. Plant,* 41, 345-363 (2005)). In addition, biotechnology can be used for the diversification of the sugar cane industry through the engineering of plants capable of producing valuable alternative products in addition to sucrose. For example, engineered sugar cane may be useful as a biofactory for the production of high value products such as pharmaceuticals, antibodies, industrial products, and alternative sugars (Lakshmanan et al. *In vitro Cell. Dev. Biol. Plant,* 41, 345-363 (2005); Wang et al. *Transgenic Research,* 14, 167-178 (2005); Hamerli et al., *Plant Biotech. J.,* 9, 32-37 (2011)).

One of the key requirements for the improvement and diversification of sugar cane through biotechnology is high levels of transgene expression. However, the molecular tools available for successful genetic engineering and, in particular, for driving high levels of gene expression, are relatively limited in sugar cane compared to many other plants.

Accordingly, the present invention overcomes the deficiencies in the art by providing compositions and methods that enhance transgene expression in sugar cane plants.

SUMMARY OF INVENTION

In one aspect of the invention a sugar cane plant cell comprising a recombinant nucleic acid molecule is provided, the recombinant nucleic acid molecule comprising a nucleotide sequence of interest, a promoter and the nucleotide sequence of SEQ ID NO:1, wherein the promoter is downstream of and in operative association with the nucleotide sequence of SEQ ID NO:1 and upstream of and in operative association with the nucleotide sequence of interest, further wherein the promoter is a maize polyubiquitin-1 promoter and/or a maize phosphoenolpyruvate carboxylase (PepC) promoter and the nucleotide sequence of interest is expressed at a level at least about 6 times greater than the level of expression of said nucleotide sequence of interest in a control.

In a second aspect of the invention a method of increasing the expression of a nucleotide sequence of interest in a sugar cane plant cell is provided, comprising: introducing into the sugar cane plant cell a recombinant nucleic acid molecule, the recombinant nucleic acid molecule comprising a nucleotide sequence of interest, a promoter and the nucleotide sequence of SEQ ID NO:1, wherein the promoter is downstream of and in operative association with the nucleotide sequence of SEQ ID NO:1 and upstream of and in operative association with the nucleotide sequence of interest, under conditions where the nucleotide sequence of interest is expressed, further wherein the promoter is a maize polyubiquitin-1 promoter and/or a maize PepC promoter, thereby increasing the expression of the nucleotide sequence of interest to at least about 6 times greater than the expression of said nucleotide sequence of interest in a control.

In other embodiments, the present invention provides sugar cane plant cells, plants, and plant parts, which comprise a nucleic acid molecule of the invention and/or a crop comprising a plurality of the sugar cane plants of the invention. In still other embodiments, the present invention also provides harvested products and processed products produced from a sugar cane plant cell, sugar cane plant, and/or sugar cane plant part of the invention.

BRIEF DESCRIPTION OF THE DRAWINGS

in FIG. 4A, n=5; and in FIG. 4B, n=11 (control) and n=12 (enhancer).

Figure 1:
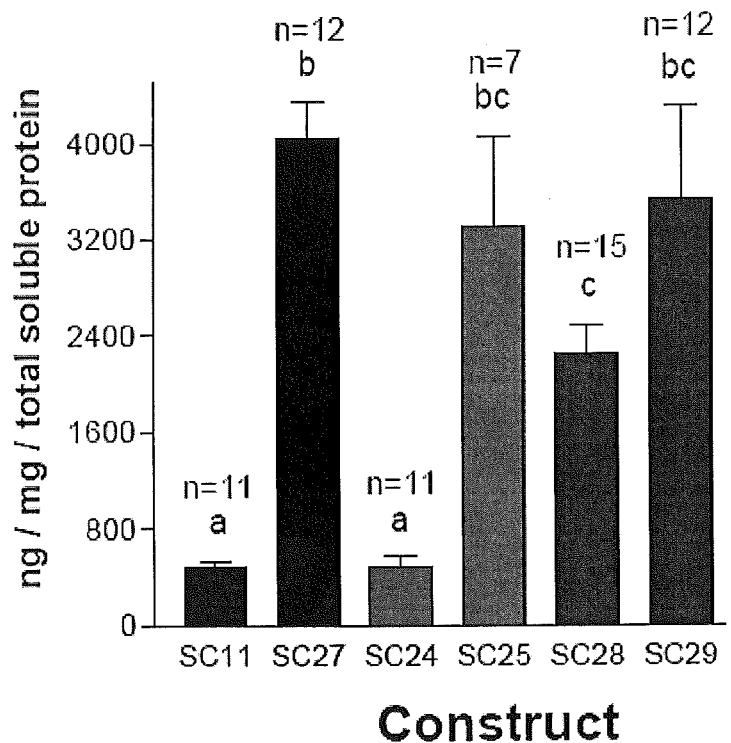
FIG. 1 shows beta-glucuronidase (GUS) expression by the different promoter-scoGUS constructs in the first unfurled leaf of six-month-old sugar cane plants. SC11 (Zm-Ubi1-scoGUS); SC27 (eFMVe35S-ZmUbi-scoGUS); SC24 (ZmPEPC-scoGUS); SC25 (eFMVe35S-ZmPEPC-scoGUS); SC28(CMP-iUbi-scoGUS); SC29 (eFMVe35S-pCMP-iUbi-scoGUS). Shown is the mean (±SEM). Data with different superscripts are significantly different ($p<0.05$).

These and other aspects of the invention are set forth in more detail in the description of the invention below.

DETAILED DESCRIPTION OF THE INVENTION

This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the present invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications and patent applications mentioned in this specification are indicative of the level of skill of those skilled in the art that this invention pertains. Further, publications, patent applications, patents, and other references mentioned herein are incorporated by reference in their entirety.

As noted previously, the molecular tools available for successful genetic manipulation of sugar cane are relatively limited compared to many other plants. In particular, achieving high levels of expression of heterologous nucleic acids has proven to be difficult and inconsistent. Evidence suggests that some of the difficulties associated with transgene expression in sugar cane may be caused by post-transcriptional gene silencing (PTGS; Mudge et al., *Planta*, 229, 549-558 (2009); Birch et al., *Tropical Plant Biol.*, 3, 88-97 (2010)). In these cases, the activity of a number of promoters has been shown to be significantly reduced in maturing sugar cane. A number of promoters have been demonstrated to be capable of expression of heterologous nucleic acids in stable transgenic sugar cane. Among these, the maize polyubiquitin-1 (Zm-Ubi1) promoter is generally considered the benchmark as it has been the most consistent, thoroughly evaluated, and most commonly used promoter for genetic engineering of sugar cane (Grof et al., (1996) *Molecular manipulation of sucrose phosphate synthase in sugarcane*. In J. R. Wilson et al. (ed) Sugarcane: Research towards efficient and sustainable production. CSIRO Division of Tropical Crops and Pastures, Brisbane, Australia. p. 124-126; Hansom et al., (1999) *Regulation of transgene expression in sugarcane*. In: Singh V (ed) Proc. Int. Soc. Sugarcane Technol. XXIII congress. STAI, New Delhi, 278-290; McQualter et al., *Plant Biotech. J.*, 3, 29-41 (2005); Vickers et al., *Crop Sci.*, 45, 354-362 (2005); Wang et al., *Transgenic Research*, 14, 167-178 (2005); Jain et al., *Plant Cell Rep.*, 26, 581-590 (2007); Petrasovits et al., *Plant Biotech. J.*, 5, 162-172 (2007); Wu and Birch, *Plant Biotech. J.* 5, 109-117 (2007); Christy et al. *Plant Cell Rep.*, 28, 175-184 (2009); Weng et al., *Transgen. Res.*, 20, 759-772 (2011)). Nevertheless, improvements in the level of transgene expression in sugar cane over that currently achieved from Zm-Ubi1 and other promoters tested to date would be very beneficial for genetic engineering of this crop.

Thus, the present invention relates to the unexpected discovery that a sugar cane plant cell, plant and/or plant part transformed with a recombinant nucleic acid molecule comprising a nucleotide sequence of interest that is operatively associated with a promoter and the promoter is further operatively associated with the nucleotide sequence of SEQ ID NO:1, results in a transformed sugar cane plant cell, plant and/or plant part having a level of expression of the nucleotide sequence of interest that is at least about 6 times greater (e.g., about 6, 7, 8, 9, 10, 11, 12, 13, 14, 15 times greater, etc) than the level of expression of the nucleotide sequence of interest in a control sugar cane plant cell, plant and/or plant that comprises the construct that differs from that use in the test plant in that it does not comprise the nucleotide sequence of SEQ ID NO:1 (i.e., the control plant comprises the promoter and the nucleotide sequence of interest in operative association but does not comprise the enhancer (SEQ ID NO:1)).

The nucleotide sequence of SEQ ID NO:1 is a dual enhancer of transcription comprising enhancer sequences from figwort mosaic virus (eFMV) and cauliflower mosaic virus (e35S) as follows:

```
                                          (SEQ ID NO: 1)
agagcttgtggggaccagacaaaaaaggaatggtgcagaattgttaggc gcacctaccaaaagcatattgcctttattgcaaagataaagcagattcc tctagtacaagtggggaacaaaataacgtggaaaagagctgtcctgaca gcccactcactaatgcgtatgacgaacgcagtgacgaccacaaaactcg agactttcaacaaagggtaatatccggaaacctcctcggattccattg cccagctatctgtcactttattgtgaagatagtggaaaaggaaggtggc tcctacaaatgccatcattgcgataaaggaaaggctatcgttgaagatg cctagccgacagtggtcccaaagatggaccccacccacgaggagcatc gtggaaaagaagacgttccaaccacgtcttcaaagcaagtggattgat gtgatatctccactgacgtaagggatgacgaacaatcccactatccttc
```

In some embodiments, the nucleotide sequence of SEQ ID NO:1 includes nucleotide sequences having about 80% to about 100% sequence identity to SEQ ID NO:1. Thus, in some embodiments, the nucleotide sequence of SEQ ID NO:1 includes nucleotide sequences having 80%, 81%, 82%, 83%, 84%, 85%, 86%, 87%, 88%, 89%, 90%, 91%, 92%, 93%, 94%, 95%, 96%, 97%, 98%, 99%, 100% sequence identity to the nucleotide sequence of SEQ ID NO:1.

In addition to increasing the expression of a nucleotide sequence of interest to which it is operatively linked (as compared to a control), it was unexpectedly discovered that the nucleotide sequence of SEQ ID NO:1 (eFMVe35S construct) enhances transcription in sugar cane plants to a significantly higher level than when compared to its ability to enhance transcription in other plant species, such as corn. Thus, when the nucleic acid construct comprising the nucleotide sequence of SEQ ID NO:1 operatively linked to a promoter that is further operatively linked to a nucleotide sequence of interest is transformed into sugar cane, the resulting level of expression of the nucleotide sequence of interest in the sugar cane plant (as compared to a control) is 2-3 times greater than the level of enhanced transcription observed in corn (as compared to a control) that is transformed with same nucleic acid construct. This surprising discovery shows that this eFMVe35S dual enhancer (SEQ ID NO:1) is particularly well suited for use in enhancing expression in sugar cane and is a significant improvement over other methods for increasing expression of nucleotide sequences in sugar cane.

Thus, in one aspect of the invention a sugar cane plant cell comprising a recombinant nucleic acid molecule is provided, the recombinant nucleic acid molecule comprising, consisting essentially of, or consisting of a nucleotide sequence of interest, a promoter and the nucleotide sequence of SEQ ID NO:1, wherein the promoter is downstream of and in operative association with the nucleotide sequence of SEQ ID NO:1 and upstream of and in operative association with the nucleotide sequence of interest, and the nucleotide sequence of interest is expressed at a level that is at least about 6 times greater (e.g., about 6, 7, 8, 9, 10, 11, 12, 13, 14, 15 times greater, etc.) than the level of expression of said nucleotide sequence of interest in a control. In some embodiments, the promoter can be any promoter as described below. In other embodiments, the promoter is a maize polyubiquitin-1 promoter and/or a maize phosphoenolpyruvate carboxylase (PepC) promoter.

Thus, in a further aspect of the invention a sugar cane plant cell molecule comprising a recombinant nucleic acid molecule is provided, the recombinant nucleic acid molecule comprising, consisting essentially of, or consisting of a nucleotide sequence of interest, a promoter and the nucleotide sequence of SEQ ID NO:1, wherein the promoter is downstream of and in operative association with the nucleotide sequence of SEQ ID NO:1 and upstream of and in operative association with the nucleotide sequence of interest, further wherein the promoter is a maize polyubiquitin-1 promoter and/or a maize PepC promoter and the nucleotide sequence of interest is expressed at a level that is at least about 6 times greater (e.g., about 6, 7, 8, 9, 10, 11, 12, 13, 14, 15 times greater, etc.) than the level of expression of said nucleotide sequence of interest in a control.

In another aspect of the invention, a method of increasing the expression of a nucleotide sequence of interest in a sugar cane plant cell is provided, the method comprising: introducing into the sugar cane plant cell a recombinant nucleic acid molecule, the recombinant nucleic acid molecule comprising, consisting essentially of, or consisting of a nucleotide sequence of interest, a promoter and the nucleotide sequence of SEQ ID NO:1, wherein the promoter is downstream of and in operative association with the nucleotide sequence of SEQ ID NO:1 and upstream of and in operative association with the nucleotide sequence of interest, under conditions where the nucleotide sequence of interest is expressed, thereby increasing the expression of the nucleotide sequence of interest to at least about 6 times (e.g., about 6, 7, 8, 9, 10, 11, 12, 13, 14, 15 times greater, etc) greater than the expression of said nucleotide sequence of interest in a control. In some embodiments, the promoter can be any promoter as described below. In other embodiments, the promoter is a maize polyubiquitin-1 promoter and/or a maize PepC promoter.

Thus, in an additional aspect, a method of increasing the expression of a nucleotide sequence of interest in a sugar cane plant cell is provided, comprising: introducing into the sugar cane plant cell a recombinant nucleic acid molecule, the recombinant nucleic acid molecule comprising, consisting essentially of or consisting of a nucleotide sequence of interest, a promoter and the nucleotide sequence of SEQ ID NO:1, wherein the promoter is downstream of and in operative association with the nucleotide sequence of SEQ ID NO:1 and upstream of and in operative association with the nucleotide sequence of interest, under conditions where the nucleotide sequence of interest is expressed, further wherein the promoter is a maize polyubiquitin-1 promoter and/or a maize PepC promoter, thereby increasing the expression of the nucleotide sequence of interest to at least about 6 times (e.g., about 6, 7, 8, 9, 10, 11, 12, 13, 14, 15 times greater, etc) greater than the expression of said nucleotide sequence of interest in a control.

In particular embodiments, the control is a sugar cane plant comprising the same recombinant nucleic acid molecule absent the enhancer sequence (i.e., the recombinant nucleic acid molecule comprises the promoter in operative association with the nucleotide sequence of interest but does not comprise the nucleotide sequence of SEQ ID NO:1 in operative association with the promoter).

In some aspects, a recombinant nucleic acid molecule of the invention further comprises a Kozak sequence. Thus, in one embodiment of the invention, the recombinant nucleic acid molecule comprises, consists essentially of or consists of a nucleotide sequence of interest, a promoter, a Kozak sequence and the nucleotide sequence of SEQ ID NO:1, wherein the promoter is downstream of and in operative association with the nucleotide sequence of SEQ ID NO:1 and upstream of and in operative association with the nucleotide sequence of interest, and the Kozak sequence is upstream (e.g., immediately upstream) of the nucleotide sequence of interest and downstream of the promoter and in operative association with both the promoter and the nucleotide sequence of interest. Any kozak sequence can be used. In some particular embodiments, the Kozak sequence is gcggccgcc.

Additional aspects of the present invention provide sugar cane plant cells, plants and plant parts transformed with a recombinant nucleic acid molecule of the invention and products harvested from the transformed sugar cane plants and plant parts as well as processed products produced from the harvested products of the invention. Thus, a particular aspect of the invention provides a plant comprising a plant cell, the plant cell further comprising a recombinant nucleic acid molecule of the invention.

Products harvested from sugar cane include, but are not limited to, bagasse, canes, stover, and the like, and/or any combination thereof. Non-limiting examples of processed products produced from the harvested sugar cane products include pulp, paper, bagasse boards, furfural for use in resins, biofuels, including but not limited to ethanol, animal feed, foodstuffs, including but not limited to sugar, sugar cane juice, syrup, rum, molasses, and the like, and/or any combination thereof. Processed products can also be produced from sugar cane used as a biofactory. Non-limiting examples of biofactory products include enzymes, pharmaceuticals, alternative sugars, antibodies, industrial products, and the like, and/or any combination thereof.

In yet a further embodiment, the present invention provides a sugar cane crop comprising a plurality of the transgenic sugar cane plants of the invention planted together in an agricultural field.

As used in the description of the embodiments of the invention and the appended claims, the singular forms "a," "an," and "the" are intended to include the plural forms as well, unless the context clearly indicates otherwise.

As used herein, "and/or" refers to and encompasses any and all possible combinations of one or more of the associated listed items.

The term "about," as used herein when referring to a measurable value such as an amount of a compound, dose, time, temperature, and the like, is meant to encompass variations of 20%, 10%, 5%, 1%, 0.5%, or even 0.1% of the specified amount.

The terms "comprise," "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising." Thus, the term "consists essentially of" (and grammatical variants), as applied to a polynucleotide sequence of the invention, means a polynucleotide that consists of both the recited sequence (e.g., SEQ ID NO) and a total of ten or less (e.g., 1, 2, 3, 4, 5, 6, 7, 8, 9, or 10) additional nucleotides on the 5' and/or 3' ends of the recited sequence such that the function of the polynucleotide is not materially altered. The total of ten or less additional nucleotides includes the total number of additional nucleotides on both ends added together.

The terms "nucleotide sequence" "nucleic acid," "nucleic acid molecule," "oligonucleotide" and "polynucleotide" are used interchangeably herein to refer to a heteropolymer of nucleotides and encompass both RNA and DNA, including cDNA, genomic DNA, mRNA, synthetic (e.g., chemically synthesized) DNA or RNA and chimeras of RNA and DNA. The term nucleic acid refers to a chain of nucleotides without regard to length of the chain. A nucleic acid can be double-stranded or single-stranded. Where single-stranded, the nucleic acid can be a sense strand or an antisense strand. A nucleic acid can be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases. Nucleic acid sequences provided herein are presented herein in the 5' to 3' direction, from left to right and are represented using the standard code for representing the nucleotide characters as set forth in the U.S. sequence rules, 37 CFR §§1.821-1.825 and the World Intellectual Property Organization (WIPO) Standard ST.25.

As used herein, the term "gene" refers to a nucleic acid molecule capable of being used to produce mRNA, antisense RNA, miRNA, and the like. Genes may or may not be capable of being used to produce a functional protein. Genes can include both coding and non-coding regions (e.g., introns, regulatory elements, promoters, enhancers, termination sequences and 5' and 3' untranslated regions).

An "isolated" nucleic acid molecule or nucleotide sequence or an "isolated" polypeptide is a nucleic acid molecule, nucleotide sequence or polypeptide that, by the hand of man, exists apart from its native environment and is therefore not a product of nature. An isolated nucleic acid molecule or isolated polypeptide may exist in a purified form or may exist in a non-native environment such as, for example, a recombinant host cell. Thus, for example, with respect to a polynucleotide, the term "isolated" means that it is separated from the chromosome and/or cell in which it naturally occurs. A polynucleotide is also isolated if it is separated from the chromosome and/or cell in which it naturally occurs in and is then inserted into a genetic context, a chromosome and/or a cell in which it does not naturally occur. The recombinant nucleic acid molecules and nucleotide sequences of the invention can be considered to be "isolated" as defined above.

Thus, an "isolated nucleic acid molecule" or "isolated nucleotide sequence" is a nucleic acid molecule or nucleotide sequence that is not immediately contiguous with all of the nucleotide sequences with which it is immediately contiguous (one on the 5' end and one on the 3' end) in the naturally occurring genome of the organism from which it is derived. In one embodiment, an isolated nucleic acid molecule or isolated nucleotide sequence includes some or all of the 5' non-coding (e.g., promoter) sequences that are immediately contiguous to a coding sequence. The term therefore includes, for example, a recombinant nucleic acid molecule that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment), independent of other sequences. It also includes a recombinant nucleic acid that is part of a hybrid nucleic acid molecule encoding an additional polypeptide or peptide sequence.

The term "isolated" can further refer to a nucleic acid molecule, nucleotide sequence, polypeptide, peptide or fragment that is substantially free of cellular material (including but not limited to proteins such as histones), viral material, and/or culture medium (e.g., when produced by recombinant DNA techniques), or chemical precursors or other chemicals (e.g., when chemically synthesized). Moreover, an "isolated fragment" is a fragment of a nucleic acid molecule, nucleotide sequence or polypeptide that is not naturally occurring as a fragment and would not be found as such in the natural state. "Isolated" does not necessarily mean that the preparation is technically pure (homogeneous), but it is sufficiently pure to provide the polypeptide or nucleic acid in a form in which it can be used for the intended purpose.

In representative embodiments of the invention, an "isolated" nucleic acid molecule, nucleotide sequence, and/or polypeptide is at least about 5%, 10%, 15%, 20%, 25%, 30%, 40%, 50%, 60%, 70%, 75%, 80%, 85%, 90%, 95%, 97%, 98%, 99% pure (w/w) or more. In other embodiments, an "isolated" nucleic acid, nucleotide sequence, and/or polypeptide indicates that at least about a 5-fold, 10-fold, 25-fold, 100-fold, 1000-fold, 10,000-fold, 100,000-fold or more enrichment of the nucleic acid (w/w) is achieved as compared with the starting material.

As used herein, "heterologous" refers to a nucleic acid molecule or nucleotide sequence that either originates from another species or is from the same species or organism but is modified from either its original form or the form primarily expressed in the cell. Thus, a nucleotide sequence derived from an organism or species different from that of the cell into which the nucleotide sequence is introduced, is heterologous with respect to that cell and the cell's descendants. In addition, a heterologous nucleotide sequence includes a nucleotide sequence derived from and inserted into the same natural, original cell type, but which is present in a non-natural state, e.g. present in a different copy number, and/or under the control of different regulatory sequences than that found in the native state of the nucleic acid molecule.

"Wild type" nucleotide sequence or amino acid sequence refers to a naturally occurring ("native") or endogenous nucleotide sequence or amino acid sequence. Thus, for example, a "wild type mRNA" is an mRNA that is naturally occurring in or endogenous to the organism. A "homologous" nucleotide sequence is a nucleotide sequence naturally associated with a host cell into which it is introduced.

By the term "express" or "expression" of a polynucleotide coding sequence, it is meant that the sequence is transcribed, and optionally translated. Thus, in some particular embodiments of the present invention, expression of a coding sequence of the invention will result in the production of a polypeptide.

"Nucleotide sequence of interest" refers to any nucleotide sequence which, when introduced into a plant, confers upon the plant a desired characteristic such as antibiotic resistance, virus resistance, insect resistance, disease resistance, or resistance to other pests, herbicide tolerance, improved nutritional value, improved performance in an industrial process or altered reproductive capability. The "nucleotide sequence of interest" may also be one that is transferred to plants for the production of commercially valuable products such as enzymes or metabolites in the plant.

As used herein, the phrases "operably linked," "operatively linked," "operatively associated" or "in operative association," and the like mean that elements of a nucleic acid construct such as an expression cassette or nucleic acid molecule are configured so as to perform their usual function. Thus, regulatory or control sequences (e.g., promoters) operably linked to a nucleotide sequence of interest are capable of effecting expression of the nucleotide sequence of interest. Further, control sequences can be regulated by regulatory sequences such as the nucleotide sequences of the invention, e.g., SEQ ID NO:1, which when operably linked to a promoter that is in turn operably linked to the nucleotide sequence of interest can result in increased expression of the nucleotide sequence of interest as compared to expression of the nucleotide sequence of interest in a control plant (wherein the control plant is a sugar cane plant comprising the same recombinant nucleic acid molecule with the exception that in the case of the control, the recombinant nucleic acid molecule comprises the promoter and the nucleotide sequence of interest in operative association but does not comprise the nucleotide sequence of SEQ ID NO:1, and therefore does not comprise the nucleotide sequence of SEQ ID NO:1 in operative association with the promoter).

The regulatory or control sequences need not be contiguous with the nucleotide sequence of interest, so long as they function to direct the expression thereof. Thus, for example, intervening untranslated, yet transcribed, sequences can be present between a promoter and a coding sequence, and the promoter sequence can still be considered "operably linked" to the coding sequence. Thus, in some embodiments of the invention, a nucleotide sequence of interest can be operatively linked to a promoter that is operatively linked to the nucleotide sequence of SEQ ID NO:1, thereby allowing increased expression of the nucleotide sequence of interest in a plant, plant part and/or plant cell.

As used herein, the terms "transformed" and "transgenic" refer to any plant, plant cell, callus, plant tissue, or plant part that contains all or part of at least one recombinant (e.g., heterologous) polynucleotide. In some embodiments, all or part of the recombinant polynucleotide is stably integrated into a chromosome or stable extra-chromosomal element, so that it is passed on to successive generations. For the purposes of the invention, the term "recombinant polynucleotide" refers to a polynucleotide that has been altered, rearranged, or modified by genetic engineering. Examples include any cloned polynucleotide, or polynucleotides, that are linked or joined to heterologous sequences. The term "recombinant" does not refer to alterations of polynucleotides that result from naturally occurring events, such as spontaneous mutations, or from non-spontaneous mutagenesis followed by selective breeding.

Introducing" in the context of a plant cell, plant and/or plant part means contacting a nucleic acid molecule with the plant, plant part, and/or plant cell in such a manner that the nucleic acid molecule gains access to the interior of the plant cell and/or a cell of the plant and/or plant part. Where more than one nucleic acid molecule is to be introduced these nucleic acid molecules can be assembled as part of a single polynucleotide or nucleic acid construct, or as separate polynucleotide or nucleic acid constructs, and can be located on the same or different nucleic acid constructs. Accordingly, these polynucleotides can be introduced into plant cells in a single transformation event, in separate transformation events, or, e.g., as part of a breeding protocol. Thus, the term "transformation" as used herein refers to the introduction of a heterologous nucleic acid into a cell. Transformation of a cell may be stable or transient.

The term "plant part," as used herein, includes but is not limited to embryos, pollen, ovules, seeds, leaves, flowers, branches, fruit, kernels, ears, cobs, husks, stalks, roots, root tips, anthers, plant cells including plant cells that are intact in plants and/or parts of plants, plant protoplasts, plant tissues, plant cell tissue cultures, plant calli, plant clumps, and the like. Further, as used herein, "plant cell" refers to a structural and physiological unit of the plant, which comprises a cell wall and also may refer to a protoplast. In some embodiments, a plant cell can be in the form of an isolated single cell or can be a cultured cell or can be a part of a higher-organized unit such as, for example, a plant tissue or a plant organ.

"Transient transformation" in the context of a polynucleotide means that a polynucleotide is introduced into the cell and does not integrate into the genome of the cell.

As used herein, "stably introducing," "stably introduced," "stable transformation" or "stably transformed" in the context of a polynucleotide introduced into a cell, means that the introduced polynucleotide is stably integrated into the genome of the cell, and thus the cell is stably transformed with the polynucleotide. As such, the integrated polynucleotide is capable of being inherited by the progeny thereof, more particularly, by the progeny of multiple successive generations. "Genome" as used herein includes the nuclear and/or plastid genome, and therefore includes integration of a polynucleotide into, for example, the chloroplast genome. Stable transformation as used herein can also refer to a polynucleotide that is maintained extrachromasomally, for example, as a minichromosome.

Transient transformation may be detected by, for example, an enzyme-linked immunosorbent assay (ELISA) or Western blot, which can detect the presence of a peptide or polypeptide encoded by one or more nucleic acid molecules introduced into an organism. Stable transformation of a cell can be detected by, for example, a Southern blot hybridization assay of genomic DNA of the cell with nucleic acid sequences which specifically hybridize with a nucleotide sequence of a nucleic acid molecule introduced into an organism (e.g., a plant). Stable transformation of a cell can be detected by, for example, a Northern blot hybridization assay of RNA of the cell with nucleic acid sequences which specifically hybridize with a nucleotide sequence of a nucleic acid molecule introduced into a plant or other organism. Stable transformation of a cell can also be detected by, e.g., a polymerase chain reaction (PCR) or other amplification reaction as are well known in the art, employing specific primer sequences that hybridize with target sequence(s) of a nucleic acid molecule, resulting in amplification of the target sequence(s), which can be detected according to standard methods Transformation can also be detected by direct sequencing and/or hybridization protocols well known in the art.

Transformation

Procedures for transforming plants are well known and routine in the art and are described throughout the literature. Non-limiting examples of methods for transformation of plants include transformation via bacterial-mediated nucleic acid delivery (e.g., via Agrobacteria), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, polymer-mediated transformation, including but not limited to polyethylene glycol (PEG)-mediated nucleic acid uptake, as well as any other electrical, chemical, physical (mechanical) and/or biological mechanism that results in the introduction of nucleic acid into the plant cell, including any combination thereof. General guides to various plant transformation methods known in the art include Mild et al. ("Procedures for Introducing Foreign DNA into Plants" in *Methods in Plant Molecular Biology and Biotechnology*, Glick, B. R. and Thompson, J. E., Eds. (CRC Press, Inc., Boca Raton, 1993), pages 67-88) and Rakowoczy-Trojanowska (*Cell. Mol. Biol. Lett.* 7:849-858 (2002)).

*Agrobacterium*-mediated transformation is a commonly used method for transforming plants, in particular, dicot plants, because of its high efficiency of transformation and because of its broad utility with many different species. *Agrobacterium*-mediated transformation typically involves transfer of the binary vector carrying the foreign DNA of interest to an appropriate *Agrobacterium* strain that may depend on the complement of vir genes carried by the host *Agrobacterium* strain either on a co-resident Ti plasmid or chromosomally (Uknes et al. (1993) *Plant Cell* 5:159-169). The transfer of the recombinant binary vector to *Agrobacterium* can be accomplished by a triparental mating procedure using *Escherichia coli* carrying the recombinant binary vector, a helper *E. coli* strain that carries a plasmid that is able to mobilize the recombinant binary vector to the target *Agrobacterium* strain. Alternatively, the recombinant binary vector can be transferred to *Agrobacterium* by nucleic acid transformation (Höfgen & Willmitzer (1988) *Nucleic Acids Res.* 16:9877).

Transformation of a plant by recombinant *Agrobacterium* usually involves co-cultivation of the *Agrobacterium* with explants from the plant and follows methods well known in the art. Transformed tissue is regenerated on selection medium carrying an antibiotic or herbicide resistance marker between the binary plasmid T-DNA borders.

Another method for transforming plants, plant parts and plant cells involves propelling inert or biologically active particles at plant tissues and cells. See, e.g., U.S. Pat. Nos. 4,945,050; 5,036,006 and 5,100,792. Generally, this method involves propelling inert or biologically active particles at the plant cells under conditions effective to penetrate the outer surface of the cell and afford incorporation within the interior thereof. When inert particles are utilized, the vector can be introduced into the cell by coating the particles with the vector containing the nucleic acid of interest. Alternatively, a cell or cells can be surrounded by the vector so that the vector is carried into the cell by the wake of the particle. Biologically active particles (e.g., a dried yeast cell, a dried bacterium or a bacteriophage, each containing one or more nucleic acids sought to be introduced) also can be propelled into plant tissue.

Thus, in particular embodiments of the present invention, a plant cell can be transformed by any method known in the art and intact plants can be regenerated from these transformed cells using any of a variety of known techniques. Thus, in some embodiments, a plant cell transformed with a nucleic acid molecule of the invention can be regenerated by methods well known in the art to produce a transformed plant or plant part of the invention. Plant regeneration from plant cells, plant tissue culture and/or cultured protoplasts is described, for example, in Evans et al. (*Handbook of Plant Cell Cultures*, Vol. 1, MacMilan Publishing Co. New York (1983)); and Vasil I. R. (ed.) (*Cell Culture and Somatic Cell Genetics of Plants*, Acad. Press, Orlando, Vol. I (1984), and Vol. II (1986)). Methods of selecting for transformed, transgenic plants, plant cells and/or plant tissue culture are routine in the art and can be employed in the methods of the invention provided herein.

Likewise, in some embodiments, the genetic properties engineered into the transgenic seeds and plants, plant parts, and/or plant cells of the present invention described above can be passed on by sexual reproduction or vegetative growth and therefore can be maintained and propagated in progeny plants. Generally, maintenance and propagation make use of known agricultural methods developed to fit specific purposes such as harvesting, sowing or tilling.

A nucleotide sequence therefore can be introduced into the plant, plant part and/or plant cell in any number of ways that are well known in the art. The methods of the invention do not depend on a particular method for introducing one or more nucleotide sequences into a plant, only that they gain access to the interior of at least one cell of the plant. Where more than one nucleotide sequence is to be introduced, the respective nucleotide sequences can be assembled as part of a single nucleic acid construct/molecule, or as separate nucleic acid constructs/molecules, and can be located on the same or different nucleic acid constructs/molecules. Accordingly, the nucleotide sequences can be introduced into a cell in a single transformation event, in separate transformation events, or, for example, in plants, as part of a breeding protocol.

In some embodiments of this invention, the introduced nucleic acid molecule may be maintained in the plant cell stably if it is incorporated into a non-chromosomal autonomous replicon or integrated into the plant chromosome(s). Alternatively, the introduced nucleic acid molecule may be present on an extra-chromosomal non-replicating vector and be transiently expressed or transiently active. Whether present in an extra-chromosomal non-replicating vector or a vector that is integrated into a chromosome, the nucleic acid molecule can be present in a plant expression cassette.

Nucleic Acid Constructs

A plant expression cassette or nucleic acid molecule can contain regulatory sequences (in addition to the nucleotide sequence of SEQ ID NO:1) that drive gene expression in plant cells that are operably linked so that each sequence can fulfill its function, for example, termination of transcription by polyadenylation signals. Exemplary polyadenylation signals can be those originating from *Agrobacterium tumefaciens* T-DNA such as the gene known as octopine synthase of the Ti-plasmid pTiACH5 (Gielen et al. *EMBO J.* 3:835 (1984)) or functional equivalents thereof, but also all other terminators functionally active in plants are suitable.

Thus, some embodiments of the invention are directed to expression cassettes designed to express the nucleotide sequences and nucleic acid molecules of the present invention. As used herein, "expression cassette" means a nucleic acid molecule having at least a control sequence operatively linked to a nucleotide sequence of interest. In this manner, for example, plant promoters in operable interaction or associated with the nucleotide sequences to be expressed are provided in expression cassettes for expression in a plant, plant part and/or plant cell.

As used herein, the term "promoter" refers to a region of a nucleotide sequence that incorporates the necessary signals for the efficient expression of a coding sequence operatively associated with the promoter. This may include sequences to which an RNA polymerase binds, but is not limited to such sequences and can include regions to which other regulatory proteins bind, together with regions involved in the control of protein translation and can also include coding sequences. Furthermore, a "promoter" of this invention is a promoter (e.g., a nucleotide sequence) capable of initiating transcription of a nucleic acid molecule in a cell of a plant.

The choice of promoters useable with the present invention can be made among many different types of promoters. Thus, the choice of promoter depends upon several factors, including, but not limited to, cell- or tissue-specific expression, desired expression level, efficiency, inducibility and/or selectability. For example, where expression in a specific tissue or organ is desired in addition to inducibility, a tissue-specific promoter can be used (e.g., a root specific promoter). In contrast, where expression in response to a stimulus is desired a promoter inducible by other stimuli or chemicals can be used. Where continuous expression is desired throughout the cells of a plant a constitutive promoter can be chosen.

Non-limiting examples of constitutive promoters include cestrum virus promoter (cmp) (U.S. Pat. No. 7,166,770), the rice actin 1 promoter (Wang et al. (1992) *Mol. Cell. Biol.* 12:3399-3406; as well as U.S. Pat. No. 5,641,876), CaMV 35S promoter (Odell et al. (1985) *Nature* 313:810-812), CaMV 19S promoter (Lawton et al. (1987) *Plant Mol. Biol.* 9:315-324), nos promoter (Ebert et al. (1987) *Proc. Natl. Acad. Sci USA* 84:5745-5749), Adh promoter (Walker et al. (1987) *Proc. Natl. Acad. Sci. USA* 84:6624-6629), sucrose synthase promoter (Yang & Russell (1990) *Proc. Natl. Acad. Sci. USA* 87:4144-4148), and the ubiquitin promoter.

Some non-limiting examples of tissue-specific promoters useable with the present invention include those encoding the seed storage proteins (such as β-conglycinin, cruciferin, napin and phaseolin), zein or oil body proteins (such as oleosin), or proteins involved in fatty acid biosynthesis (including acyl carrier protein, stearoyl-ACP desaturase and fatty acid desaturases (fad 2-1)), and other nucleic acids expressed during embryo development (such as Bce4, see, e.g., Kridl et al. (1991) *Seed Sci. Res.* 1:209-219; as well as EP Patent No. 255378). Thus, in some embodiments, the promoters associated with these tissue-specific nucleic acids can be used in the present invention.

Additional examples of tissue-specific promoters include, but are not limited to, the root-specific promoters RCc3 (Jeong et al. *Plant Physiol.* 153:185-197 (2010)) and RB7 (U.S. Pat. No. 5,459,252), the lectin promoter (Lindstrom et al. (1990) *Der. Genet.* 11:160-167; and Vodkin (1983) *Prog. Clin. Biol. Res.* 138:87-98), corn alcohol dehydrogenase 1 promoter (Dennis et al. (1984) *Nucleic Acids Res.* 12:3983-4000), S-adenosyl-L-methionine synthetase (SAMS) (Vander Mijnsbrugge et al. (1996) *Plant and Cell Physiology*, 37(8):1108-1115), corn light harvesting complex promoter (Bansal et al. (1992) *Proc. Natl. Acad. Sci. USA* 89:3654-3658), corn heat shock protein promoter (O'Dell et al. (1985) *EMBO J.* 5:451-458; and Rochester et al. (1986) *EMBO J.* 5:451-458), pea small subunit RuBP carboxylase promoter (Cashmore, "Nuclear genes encoding the small subunit of ribulose-1,5-bisphosphate carboxylase" 29-39 In: *Genetic Engineering of Plants* (Hollaender ed., Plenum Press 1983; and Poulsen et al. (1986) *Mol. Gen. Genet.* 205:193-200), Ti plasmid mannopine synthase promoter (Langridge et al. (1989) *Proc. Natl. Acad. Sci. USA* 86:3219-3223), Ti plasmid nopaline synthase promoter (Langridge et al. (1989), supra), petunia chalcone isomerase promoter (van Tunen et al. (1988) *EMBO J.* 7:1257-1263), bean glycine rich protein 1 promoter (Keller et al. (1989) *Genes Dev.* 3:1639-1646), truncated CaMV 35S promoter (O'Dell et al. (1985) *Nature* 313:810-812), potato patatin promoter (Wenzler et al. (1989) *Plant Mol. Biol.* 13:347-354), root cell promoter (Yamamoto et al. (1990) *Nucleic Acids Res.* 18:7449), maize zein promoter (Kriz et al. (1987) *Mol. Gen. Genet.* 207:90-98; Langridge et al. (1983) *Cell* 34:1015-1022; Reina et al. (1990) *Nucleic Acids Res.* 18:6425; Reina et al. (1990) *Nucleic Acids Res.* 18:7449; and Wandelt et al. (1989) *Nucleic Acids Res.* 17:2354), globulin-1 promoter (Belanger et al. (1991) *Genetics* 129:863-872), α-tubulin cab promoter (Sullivan et al. (1989) *Mol. Gen. Genet.* 215:431-440), PEPCase promoter (Hudspeth & Grula (1989) *Plant Mol. Biol.* 12:579-589), R gene complex-associated promoters (Chandler et al. (1989) *Plant Cell* 1:1175-1183), and chalcone synthase promoters (Franken et al. (1991) *EMBO J.* 10:2605-2612). Particularly useful for seed-specific expression is the pea vicilin promoter (Czako et al. (1992) *Mol. Gen. Genet.* 235:33-40; as well as U.S. Pat. No. 5,625,136). Other useful promoters for expression in mature leaves are those that are switched on at the onset of senescence, such as the SAG promoter from *Arabidopsis* (Gan et al. (1995) *Science* 270:1986-1988).

In addition, promoters functional in plastids can be used. Non-limiting examples of such promoters include the bacteriophage T3 gene 9 5' UTR and other promoters disclosed in U.S. Pat. No. 7,579,516. In other embodiments, promoters useful with the present invention include but are not limited to the S-E9 small subunit RuBP carboxylase promoter and the Kunitz trypsin inhibitor gene promoter (Kti3).

In some instances, inducible promoters are useable with the present invention. Examples of inducible promoters useable with the present invention include, but are not limited to, tetracycline repressor system promoters, Lac repressor system promoters, copper-inducible system promoters, salicylate-inducible system promoters (e.g., the PR1a system), glucocorticoid-inducible promoters (Aoyama et al. (1997) *Plant J.* 11:605-612), and ecdysone-inducible system promoters. Other non-limiting examples of inducible promoters include ABA- and turgor-inducible promoters, the auxin-binding protein gene promoter (Schwob et al. (1993) *Plant J.* 4:423-432), the UDP glucose flavonoid glycosyl-transferase promoter (Ralston et al. (1988) *Genetics* 119:185-197), the MPI proteinase inhibitor promoter (Cordero et al. (1994) *Plant J.* 6:141-150), the glyceraldehyde-3-phosphate dehydrogenase promoter (Kohler et al. (1995) *Plant Mol. Biol.* 29:1293-1298; Martinez et al. (1989) *J. Mol. Biol.* 208:551-565; and Quigley et al. (1989) *J. Mol. Evol.* 29:412-421) the benzene sulphonamide-inducible promoters (U.S. Pat. No. 5,364,780) and the glutathione S-transferase promoters. Likewise, one can use any appropriate inducible promoter described in Gatz (1996) *Current Opinion Biotechnol.* 7:168-172 and Gatz (1997) *Annu. Rev. Plant Physiol. Plant Mol. Biol.* 48:89-108.

As described above, the enhancer (e.g., SEQ ID NO:1) can be used with any promoter known to those of skill in the art for expression of a nucleotide sequence of interest in a sugar cane plant. In particular embodiments, an enhancer of the invention (e.g., SEQ ID NO:1) is operatively linked to a maize polyubiquitin-1 promoter and/or a maize PepC promoter, which in turn is operatively linked to a nucleotide sequence of interest.

In addition to the enhancer (e.g., SEQ ID NO:1) and promoters described above, the expression cassette also can include other regulatory sequences. As used herein, "regulatory sequences" means nucleotide sequences located upstream (5' non-coding sequences), within or downstream (3' non-coding sequences) of a coding sequence, and which influence the transcription, RNA processing or stability, or translation of the associated coding sequence. In addition to promoters, regulatory sequences include, but are not limited to, additional enhancers, introns, kozak sequences, translation leader sequences and polyadenylation signal sequences.

A number of non-translated leader sequences derived from viruses are known to enhance gene expression. Specifically, leader sequences from Tobacco Mosaic Virus (TMV, the "ω-sequence"), Maize Chlorotic Mottle Virus (MCMV) and Alfalfa Mosaic Virus (AMV) have been shown to be effective in enhancing expression (Gallie et al. (1987) *Nucleic Acids Res.* 15:8693-8711; and Skuzeski et al. (1990) *Plant Mol. Biol.* 15:65-79). Other leader sequences known in the art include, but are not limited to, picornavirus leaders such as an encephalomyocarditis (EMCV) 5' non-coding region leader (Elroy-Stein et al. (1989) *Proc. Natl. Acad. Sci. USA* 86:6126-6130); potyvirus leaders such as a Tobacco Etch Virus (TEV) leader (Allison et al. (1986) *Virology* 154:9-20); Maize Dwarf Mosaic Virus (MDMV) leader (Allison et al. (1986), supra); human immunoglobulin heavy-chain binding protein (BiP) leader (Macejak & Samow (1991) *Nature* 353:90-94); untranslated leader from the coat protein mRNA of AMV (AMV RNA 4; Jobling & Gehrke (1987) *Nature* 325:622-625); tobacco mosaic TMV leader (Gallie et al. (1989) *Molecular Biology of RNA* 237-256); and MCMV leader (Lommel et al. (1991) *Virology* 81:382-385). See also, Della-Cioppa et al. (1987) *Plant Physiol.* 84:965-968.

An expression cassette also can optionally include a transcriptional and/or translational termination region (i.e., termination region) that is functional in plants. A variety of transcriptional terminators are available for use in expression cassettes and are responsible for the termination of transcription beyond the heterologous nucleotide sequence of interest and correct mRNA polyadenylation. The termination region may be native to the transcriptional initiation region, may be native to the operatively linked nucleotide sequence of interest, may be native to the plant host, or may be derived from another source (i.e., foreign or heterologous to the promoter, the nucleotide sequence of interest, the plant host, or any combination thereof). Appropriate transcriptional terminators include, but are not limited to, the CAMV 35S terminator, the tml terminator, the nopaline synthase terminator and the pea rbcs E9 terminator. These can be used in both monocotyledons and dicotyledons. In addition, a coding sequence's native transcription terminator can be used.

In some particular embodiments, a signal sequence can be operably linked to a nucleic acid molecule of the present invention to direct the nucleic acid molecule into a cellular compartment. In this manner, the expression cassette can comprise a nucleic acid molecule of the present invention operably linked to a nucleotide sequence for the signal sequence. The signal sequence may be operably linked at the N- or C-terminus of the nucleic acid molecule.

As described above, in some embodiments, the expression cassette or nucleic acid molecule of the present invention can include a Kozak sequence, wherein the Kozak sequence is immediately upstream (e.g., immediately upstream) of the nucleotide sequence of interest and downstream of the promoter and in operative association with both the promoter and the nucleotide sequence of interest. In some particular embodiments, the Kozak sequence is gcggccgcc.

The expression cassette also can include a nucleotide sequence for a selectable marker, which can be used to select a transformed plant, plant part and/or plant cell. As used herein, "selectable marker" means a nucleotide sequence that when expressed imparts a distinct phenotype to the plant, plant part and/or plant cell expressing the marker and thus allows such transformed plants, plant parts and/or plant cells to be distinguished from those that do not have the marker. Such a nucleotide sequence may encode either a selectable or screenable marker, depending on whether the marker confers a trait that can be selected for by chemical means, such as by using a selective agent (e.g., an antibiotic, herbicide, or the like), or on whether the marker is simply a trait that one can identify through observation or testing, such as by screening (e.g., the R-locus trait). Of course, many examples of suitable selectable markers are known in the art and can be used in the expression cassettes described herein.

Examples of selectable markers include, but are not limited to, a nucleotide sequence encoding neo or nptII, which confers resistance to kanamycin, G418, and the like (Potrykus et al. (1985) *Mol. Gen. Genet.* 199:183-188); a nucleotide sequence encoding bar, which confers resistance to phosphinothricin; a nucleotide sequence encoding an altered 5-enolpyruvylshikimate-3-phosphate (EPSP) synthase, which confers resistance to glyphosate (Hinchee et al. (1988) *Biotech.* 6:915-922); a nucleotide sequence encoding a nitrilase such as bxn from *Klebsiella ozaenae* that confers resistance to bromoxynil (Stalker et al. (1988) *Science* 242:419-423); a nucleotide sequence encoding an altered acetolactate synthase (ALS) that confers resistance to imidazolinone, sulfonylurea or other ALS-inhibiting chemicals (EP Patent Application No. 154204); a nucleotide sequence encoding a methotrexate-resistant dihydrofolate reductase (DHFR) (Thillet et al. (1988) *J. Biol. Chem.* 263:12500-12508); a nucleotide sequence encoding a dalapon dehalogenase that confers resistance to dalapon; a nucleotide sequence encoding a mannose-6-phosphate isomerase (also referred to as phosphomannose isomerase (PMI)) that confers an ability to metabolize mannose (U.S. Pat. Nos. 5,767,378 and 5,994,629); a nucleotide sequence encoding an altered anthranilate synthase that confers resistance to 5-methyl tryptophan; and/or a nucleotide sequence encoding hph that confers resistance to hygromycin. One of skill in the art is capable of choosing a suitable selectable marker for use in an expression cassette of this invention.

Additional selectable markers include, but are not limited to, a nucleotide sequence encoding β-glucuronidase or uidA (GUS) that encodes an enzyme for which various chromogenic substrates are known; an R-locus nucleotide sequence that encodes a product that regulates the production of anthocyanin pigments (red color) in plant tissues (Dellaporta et al., "Molecular cloning of the maize R-nj allele by transposon-tagging with Ac" 263-282 In: *Chromosome Structure and Function: Impact of New Concepts*, 18th Stadler Genetics Symposium (Gustafson & Appels eds., Plenum Press 1988)); a nucleotide sequence encoding β-lactamase, an enzyme for which various chromogenic substrates are known (e.g., PADAC, a chromogenic cephalosporin) (Sutcliffe (1978) *Proc. Natl. Acad. Sci. USA* 75:3737-3741); a nucleotide sequence encoding xylE that encodes a catechol dioxygenase (Zukowsky et al. (1983) *Proc. Natl. Acad. Sci. USA* 80:1101-1105); a nucleotide sequence encoding tyrosinase, an enzyme capable of oxidizing tyrosine to DOPA and dopaquinone, which in turn condenses to form melanin (Katz et al. (1983) *J. Gen. Microbiol.* 129:2703-2714); a nucleotide sequence encoding β-galactosidase, an enzyme for which there are chromogenic substrates; a nucleotide sequence encoding luciferase (lux) that allows for bioluminescence detection (Ow et al. (1986) *Science* 234:856-859); a nucleotide sequence encoding aequorin which may be employed in calcium-sensitive bioluminescence detection (Prasher et al. (1985) *Biochem. Biophys. Res. Comm.* 126:1259-1268); or a nucleotide sequence encoding green fluorescent protein (Niedz et al. (1995) *Plant Cell Reports* 14:403-406). One of skill in the art is capable of choosing a suitable selectable marker for use in an expression cassette of this invention.

Nucleotide Sequences of Interest

A nucleic acid molecule or expression cassette also can include a coding sequence for one or more polypeptides for agronomic traits that primarily are of benefit to a seed company, grower or grain processor. A polypeptide of interest can be any polypeptide encoded by a nucleotide sequence of interest. Non-limiting examples of polypeptides of interest that are suitable for production in plants include those resulting in agronomically important traits such as herbicide resistance (also sometimes referred to as "herbicide tolerance"), virus resistance, bacterial pathogen resistance, insect resistance, nematode resistance, and/or fungal resistance. See, e.g., U.S. Pat. Nos. 5,569,823; 5,304,730; 5,495,071; 6,329,504; and 6,337,431. The polypeptide also can be one that increases plant vigor or yield (including traits that allow a plant to grow at different temperatures, soil conditions and levels of sunlight and precipitation), or one that allows identification of a plant exhibiting a trait of interest (e.g., a selectable marker, seed coat color, etc.). Various polypeptides of interest, as well as methods for introducing these polypeptides into a plant, are described, for example, in U.S. Pat. Nos. 4,761,373; 4,769,061; 4,810,648; 4,940,835; 4,975,374; 5,013,659; 5,162,602; 5,276,268; 5,304,730; 5,495,071; 5,554,798; 5,561,236; 5,569,823; 5,767,366; 5,879,903; 5,928,937; 6,084,155; 6,329,504 and 6,337,431; as well as US Patent Publication No. 2001/0016956. See also, on the World Wide Web at lifesci.sussex.ac.uk/home/Neil_Crickmore/Bt/.

Nucleotide sequences conferring resistance/tolerance to an herbicide that inhibits the growing point or meristem, such as an imidazalinone or a sulfonylurea can also be suitable in some embodiments of the invention. Exemplary nucleotide sequences in this category code for mutant ALS and AHAS enzymes as described, e.g., in U.S. Pat. Nos. 5,767,366 and 5,928,937. U.S. Pat. Nos. 4,761,373 and 5,013,659 are directed to plants resistant to various imidazalinone or sulfonamide herbicides. U.S. Pat. No. 4,975,374 relates to plant cells and plants containing a nucleic acid encoding a mutant glutamine synthetase (GS) resistant to inhibition by herbicides that are known to inhibit GS, e.g., phosphinothricin and methionine sulfoximine. U.S. Pat. No. 5,162,602 discloses plants resistant to inhibition by cyclohexanedione and aryloxyphenoxypropanoic acid herbicides. The resistance is conferred by an altered acetyl coenzyme A carboxylase (ACCase).

Polypeptides encoded by nucleotides sequences conferring resistance to glyphosate are also suitable for use with the present invention. See, e.g., U.S. Pat. No. 4,940,835 and U.S. Pat. No. 4,769,061. U.S. Pat. No. 5,554,798 discloses transgenic glyphosate resistant maize plants, which resistance is conferred by an altered 5-enolpyruvyl-3-phosphoshikimate (EPSP) synthase gene.

Nucleotide sequences coding for resistance to phosphono compounds such as glufosinate ammonium or phosphinothricin, and pyridinoxy or phenoxy propionic acids and cyclohexones are also suitable. See, European Patent Application No. 0 242 246. See also, U.S. Pat. Nos. 5,879,903, 5,276,268 and 5,561,236.

Other suitable nucleotide sequences include those coding for resistant to herbicides that inhibit photosynthesis, such as a triazine and a benzonitrile (nitrilase). See, U.S. Pat. No. 4,810,648. Additional suitable nucleotide sequences coding for herbicide resistance include those coding for resistance to 2,2-dichloropropionic acid, sethoxydim, haloxyfop, imidazolinone herbicides, sulfonylurea herbicides, triazolopyrimidine herbicides, s-triazine herbicides and bromoxynil. Also suitable are nucleotide sequences conferring resistance to a protox enzyme, or that provide enhanced resistance to plant diseases; enhanced tolerance of adverse environmental conditions (abiotic stresses) including but not limited to drought, excessive cold, excessive heat, or excessive soil salinity or extreme acidity or alkalinity; and alterations in plant architecture or development, including changes in developmental timing. See, e.g., U.S. Patent Publication No. 2001/0016956 and U.S. Pat. No. 6,084,155.

Insecticidal proteins useful in the invention may be produced in an amount sufficient to control insect pests, i.e., insect controlling amounts. It is recognized that the amount of production of insecticidal protein in a plant necessary to control insects may vary depending upon the cultivar, type of insect, environmental factors and the like. Nucleotide sequences useful for insect or pest resistance include, for example, those that encode toxins identified in *Bacillus* organisms. Nucleotide sequences encoding *Bacillus thuringiensis* (Bt) toxins from several subspecies have been cloned and recombinant clones have been found to be toxic to lepidopteran, dipteran and coleopteran insect larvae (for example, various delta-endotoxin genes such as Cry1Aa, Cry1Ab, Cry1Ac, Cry1B, Cry1C, Cry1D, Cry1Ea, Cry1Fa, Cry3A, Cry9A, Cry9C and Cry9B; as well as genes encoding vegetative insecticidal proteins such as Vip2 and Vip3). A full list of Bt toxins can be found on the worldwide web at *Bacillus thuringiensis* Toxin Nomenclature Database maintained by the University of Sussex (see also, Crickmore et al. (1998) *Microbiol. Mol. Biol. Rev.* 62:807-813).

Polypeptides that are suitable for production in plants further include those that improve or otherwise facilitate the conversion of harvested plants and/or plant parts into a commercially useful product, including, for example, increased or altered carbohydrate content and/or distribution, improved fermentation properties, increased oil content, increased protein content, improved digestibility, and increased nutraceutical content, e.g., increased phytosterol content, increased tocopherol content, increased stanol content and/or increased vitamin content. Polypeptides of interest also include, for example, those resulting in or contributing to a reduced content of an unwanted component in a harvested crop, e.g., phytic acid, or sugar degrading enzymes. By "resulting in" or "contributing to" is intended that the polypeptide of interest can directly or indirectly contribute to the existence of a trait of interest (e.g., increasing cellulose degradation by the use of a heterologous cellulase enzyme).

In one embodiment, the polypeptide of interest contributes to improved digestibility for food or feed. Xylanases are hemicellulolytic enzymes that improve the breakdown of plant cell walls, which leads to better utilization of the plant nutrients by an animal. This leads to improved growth rate and feed conversion. Also, the viscosity of the feeds containing xylan can be reduced by xylanases. Heterologous production of xylanases in plant cells also can facilitate lignocellulosic conversion to fermentable sugars in industrial processing.

Numerous xylanases from fungal and bacterial microorganisms have been identified and characterized (see, e.g., U.S. Pat. No. 5,437,992; Coughlin et al. (1993) "Proceedings of the Second TRICEL Symposium on *Trichoderma reesei* Cellulases and Other Hydrolases" Espoo; Souminen and Reinikainen, eds. (1993) *Foundation for Biotechnical and Industrial Fermentation Research* 8:125-135; U.S. Patent Publication No. 2005/0208178; and PCT Publication No. WO 03/16654). In particular, three specific xylanases (XYL-I, XYL-II, and XYL-III) have been identified in *T. reesei* (Tenkanen et al. (1992) *Enzyme Microb. Technol.* 14:566; Torronen et al. (1992) *Bio/Technology* 10:1461; and Xu et al. (1998) *Appl. Microbiol. Biotechnol.* 49:718).

In another embodiment, a polypeptide useful for the present invention can be a polysaccharide degrading enzyme. Plants of this invention producing such an enzyme may be useful for generating, for example, fermentation feedstocks for bioprocessing. In some embodiments, enzymes useful for a fermentation process include alpha amylases, proteases, pullulanases, isoamylases, cellulases, hemicellulases, xylanases, cyclodextrin glycotransferases, lipases, phytases, laccases, oxidases, esterases, cutinases, granular starch hydrolyzing enzyme and other glucoamylases.

Polysaccharide-degrading enzymes include: starch degrading enzymes such as α-amylases (EC 3.2.1.1), glucuronidases (E.C. 3.2.1.131); exo-1,4-α-D glucanases such as amyloglucosidases and glucoamylase (EC 3.2.1.3), β-amylases (EC 3.2.1.2), α-glucosidases (EC 3.2.1.20), and other exo-amylases; starch debranching enzymes, such as a) isoamylase (EC 3.2.1.68), pullulanase (EC 3.2.1.41), and the like; b) cellulases such as exo-1,4-3-cellobiohydrolase (EC 3.2.1.91), exo-1,3-β-D-glucanase (EC 3.2.1.39), β-glucosidase (EC 3.2.1.21); c) L-arabinases, such as endo-1,5-α-L-arabinase (EC 3.2.1.99), α-arabinosidases (EC 3.2.1.55) and the like; d) galactanases such as endo-1,4-β-D-galactanase (EC 3.2.1.89), endo-1,3-β-D-galactanase (EC 3.2.1.90), α-galactosidase (EC 3.2.1.22), β-galactosidase (EC 3.2.1.23) and the like; e) mannanases, such as endo-1,4-β-D-mannanase (EC 3.2.1.78), β-mannosidase (EC 3.2.1.25), α-mannosidase (EC 3.2.1.24) and the like; xylanases, such as endo-1,4-β-xylanase (EC 3.2.1.8), β-D-xylosidase (EC 3.2.1.37), 1,3-β-D-xylanase, and the like; and g) other enzymes such as α-L-fucosidase (EC 3.2.1,51), α-L-rhamnosidase (EC 3.2.1.40), levanase (EC 3.2.1.65), inulanase (EC 3.2.1.7), and the like.

Further enzymes which may be used with the present invention include proteases, such as fungal and bacterial proteases. Fungal proteases include, but are not limited to, those obtained from *Aspergillus, Trichoderma, Mucor* and *Rhizopus*, such as *A. niger, A. awamori, A. oryzae* and *M. miehei*. In some embodiments, the polypeptides of this invention can be cellobiohydrolase (CBH) enzymes (EC 3.2.1.91). In one embodiment, the cellobiohydrolase enzyme can be CBH1 or CBH2.

Other useful enzymes include, but are not limited to, hemicellulases, such as mannases and arabinofuranosidases (EC 3.2.1.55); ligninases; lipases (e.g., E.C. 3.1.1.3), glucose oxidases, pectinases, xylanases, transglucosidases, alpha 1,6 glucosidases (e.g., E.C. 3.2.1.20); esterases such as ferulic acid esterase (EC 3.1.1.73) and acetyl xylan esterases (EC 3.1.1.72); and cutinases (e.g. E.C. 3.1.1.74).

Nucleotide sequences of interest can also include nucleotide sequences encoding functional nucleic acids including, but not limited to, ribozymes, siRNA, shRNA and/or miRNA.

The present invention will now be described with reference to the following examples. It should be appreciated that these examples are not intended to limit the scope of the claims to the invention, but are rather intended to be exemplary of certain embodiments. Any variations in the exemplified methods that occur to the skilled artisan are intended to fall within the scope of the present invention.

EXAMPLES

Example 1

Production of Constructs

All polymerase chain reactions (PCR) were carried out using KAPAHiFi DNA polymerase (Geneworks), and the resulting PCR products were cloned into pGEM-T (Promega) and sequence verified prior to subcloning. Each of the constructs possess the following features:
(1) The beta-glucoronidase (GUS) coding sequence that is optimized for expression in sugar cane (scoGUS; Geneart® optimization)
(2) A Kozak sequence (gcggccgcc), which was placed immediately upstream of the scoGUS coding sequence
(3) A TMVΩ translational enhancer sequence, which was placed immediately upstream of the Kozak (gtattttacaacaattaccaacaacaacaaacaacaaacaacattac aattactatttacaattaca, SEQ ID NO: 2)

The scoGUS, TMVΩ and Kozak sequences, together with the nopaline synthase (nos) terminator, were made synthetically, and included restriction enzyme sites at each end for cloning. The TMVΩ, kozak, scoGUS gene, and nos terminator were subcloned into pBluescript using PstI and SacII to generate scoGUS/pBS. The dual transcriptional enhancer sequences from figwort mosaic virus (eFMV) and cauliflower mosaic virus (e35S) were made synthetically, and included restriction enzyme sites at each end for cloning.

Construct SC11 was generated as follows: The maize ubiquitin promoter (ZmUbi), which consists of 1993 by of sequence directly upstream of the polyubiquitin translational start site and includes the 1010 by intron in the 5' untranslated region (UTR), was amplified using PCR (adding a HindIII site at the 5' end and a PstI site at the 3' end), cloned into pGEM-T, and sequence verified. ZmUbi was subsequently subcloned into scoGUS/pBS using HindIII and PstI to generate the ZmUbi-scoGUS plasmid. The ZmUbi-scoGUS and nos sequence were subcloned into the binary construct UbinptIINos(S) using HindIII and AscI to generate construct SC11.

Construct SC24 was generated as follows: The maize phosphoenolpyruvate carboxylase promoter (ZmPEPC), which consists of 2423 by of sequence directly upstream of the PepC translational start site, the first exon, the first intron, and 20 by of the second exon, was amplified using PCR (adding a HindIII site at the 5' end and a PstI site at the 3' end), cloned into pGEM-T, and sequence verified. ZmPEPC was subsequently subcloned into scoGUS/pBS using HindIII and PstI to generate the ZmPEPC-scoGUS plasmid. The ZmPEPC-scoGUS and nos sequence were subcloned into the binary construct UbinptIINos(S) using HindIII and AscI to generate construct SC24.

Construct SC25 was generated as follows: The dual transcriptional enhancer (eFMVe35S) was subcloned into the ZmPEPC-scoGUS plasmid using HindIII and SwaI to generate the eFMVe35S-ZmPEPC-scoGUS plasmid. The eFMVe35S-ZmPEPC-scoGUS and nos sequence were subcloned into the binary construct UbinptIINos(S) using HindIII and AscI to generate construct SC25.

Construct SC27 was generated as follows: The dual transcriptional enhancer (eFMVe35S) was subcloned into the ZmUbi-scoGUS plasmid using HindIII and SwaI to generate the eFMVe35S-ZmUbi-scoGUS plasmid. The eFMVe35S-ZmUbi-scoGUS and nos sequence were subcloned into the binary construct UbinptIINos(S) using HindIII and AscI to generate construct SC27.

Construct SC28 was generated as follows: The maize ubiquitin intron (1010 bp), along with 40 bp of 5' flanking exon sequence (iUbi) were excised as a BglII and BamHI fragment and cloned into the BamHI site of plasmid pCMP-PMI/pBS (containing the 397 bp cestrum viral promoter sequence, pCMP) to generate pCMP-iUbi-PMI/pBS. The pCMP-iUbi sequence was cloned by PCR from pCMP-iUbi-PMI/pBS (adding restriction enzyme sites for HindIII and SwaI at the 5' end and a PstI site at the 3' end). The pCMP-iUbi sequence was subcloned into scoGUS/pBS using HindII and PstI. The pCMP-iUbi-scoGUS and nos sequence were subcloned into the binary construct UbinptIINos(S) using HindIII and AscI to generate construct SC28.

Construct SC29 was generated as follows: The dual transcriptional enhancer (eFMVe35S) was subcloned into the pCMP-iUbi-scoGUS plasmid using HindIII and SwaI to generate the eFMVe35S-pCMP-iUbi-scoGUS plasmid. The eFMVe35S-pCMP-iUbi-scoGUS and nos sequence were subcloned into the binary construct UbinptIINos(S) using HindIII and AscI to generate construct SC29.

A list of the constructs is provided in Table 1.

TABLE 1

List of optimised promoter-GUS constructs

| Construct ID | Construct |
|---|---|
| SC11 | ZmUbi - scoGUS |
| SC24 | ZmPEPC - scoGUS |
| SC25 | eFMVe35S - ZmPEPC - scoGUS |
| SC27 | eFMVe35S - ZmUbi - scoGUS |
| SC28 | pCMP - ZmiUbi - scoGUS |
| SC29 | eFMVe35S - pCMP - ZmiUbi - scoGUS |

Example 2

Agrobacterium-Mediated Transformation of Sugar Cane

The binary constructs were transferred into Agrobacterium strain AGL1 using a standard heat shock transformation method. Agrobacterium containing each of the binary constructs were used to transform sugar cane using following methods.

Plant Source and Material:

Leaf whorl material from field grown sugar cane plants was collected and initiated on EM3 medium (see below). Transverse sections (approximately 20) of immature leaf whorl between 1-3 mm in thickness were taken from just above the meristem and placed in the top-up orientation. Cultures were maintained in the dark at 25° C. for 28 to 42 days. Callus utilized for transformation was within 4-10 days of the last subculture. Callus was selected on morphological characteristics such as compact structure and yellow color. Yellow embryogenic calli were selected wherever possible, as they provided good regeneration, consistent transformation, and fragmented in small clusters (2-4 mm).

Infection and Co-Cultivation:

Callus tissue was heat shocked at 45° C. for 5 minutes by adding 50 ml of pre-warmed ½ strength MS medium (without sucrose) and then maintaining the callus in a water bath at 45° C. MS medium was then drained from the callus tissue, and 25 ml of the Agrobacterium inoculation suspension was added to each vessel and mixed gently. The callus/Agrobacterium mixture was vacuum-infiltrated by placing it into a vacuum chamber for 10 minutes at −27.5 mmHg. The callus/Agrobacterium mixture was then rested for 5-10 minutes in the dark.

The Agrobacterium inoculation suspension was then drained from the callus, and the remaining callus culture was blotted dry to remove excess Agrobacterium inoculation suspension. Plant tissues were blotted on filter paper such as Whatman Grade 1 paper, until the Agrobacterium inoculation suspension was substantially removed. The callus was then transferred for co-cultivation to 90×25-mm petri dishes containing no co-culture medium or containing dry filter papers or filter papers wet with sterile water, and sealed with NESCOFILM®, MICROPORE™ tape (3M; Minneapolis, Minn.) or similar material. The dishes were incubated in the dark at 22° C. for 2-3 days.

Post-Transformation:

After co-cultivation, the callus tissue was transferred to MS 1 medium (see below) containing with 200 mg/L of timentin ("resting" medium) and kept in the dark at 25° C. for 4 days. The first selection step was made in MS 2 medium (see below) containing 50 mg/L of geneticin and 200 mg/L of timentin for 14-15 days in the dark at 25° C.

Regeneration and Rooting:

Regeneration was conducted on MS 3 medium (see below) supplemented with 50 mg/L of geneticin and 200 mg/L of timentin at 25° C. in 16 hr light. Gradual increases in light intensity were required. For the first week, the culture was left on a laboratory bench under normal room lighting, and for the next 3 weeks, the culture was grown at moderate light intensity. Shoot formation was seen between 2-4 weeks. When the first leaves appeared, the shoots were transferred to MS 4 medium (see below) until the plants grew to 4-5 cm in height.

Transformed plants were initially moved from tissue culture and placed in seedling trays containing soil and incubated in a growth chamber. At approximately six to eight weeks of age, the plants were moved to 30 cm pots until maturity.

Media:

The components within the media referred to above are as follows.

EM3: MS salts and vitamins; 0.5 g/L casein hydrolysate; 100 ml/L coconut water; 20 g/L sucrose and 3 mg/l 2,4-D, solidified with 7 g/L agar.

LB basic: 10 g/L NaCl; 5 g/L yeast extract; and 10 g/L tryptone.

LB solid: LB basic with 15 g/L of agar.

MS basic: MS medium salts and vitamins, with 25 g/L sucrose.

MS 1: MS basic supplemented with 0.25 g/L casein hydrolysate; 40 ml of coconut water, 3.0 mg/L 2,4-D and 200 mg/L Timentin solidified with 7 g/L agar.

MS 2: MS basic supplemented with 0.25 g/L casein hydrolysate; 40 ml of coconut water, 3.0 mg/L 2,4-D, 50 mg/L Geneticin and 200 mg/L Timentin, solidified with 7 g/L agar.

MS 3: MS basic supplemented with 40 ml of coconut water and 0.5 mg/L $CuSO_4$, 1.0-2.0 mg/L BAP (cultivar dependent, thus not required for all cultivars) and 50 mg/L Geneticin and 200 mg/L Timentin, solidified with 7 g/L agar.

MS 4: MS basic supplemented with 1.0 g/L charcoal and 1.0 mg IBA (indole-3-butyric acid, not required for all cultivars and 50 mg/L Geneticin, solidified with 7 g/L agar.

Example 3

Characterization of Transgenic Sugar Cane Plants

Plants were screened for the presence of the nptII and scoGUS genes using TaqMan® analysis. Only plants determined to contain either 1 or 2 copies of the transgenic construct were selected for further analysis.

Sugar cane tissue samples used for quantitative analysis of GUS expression were obtained from either leaf (first unfurled leaf of 6 month old plants or first unfurled leaf of sugar cane tillers of 11 month old plants) or stem (at 12 months). The patterns of gene expression and metabolic activity vary along the length of the sugar cane stem, with younger internodes invested in processes related to growth and development, and mature internodes at the base of the plant primarily focused on sucrose storage (Casu et al., *Plant Mol. Biol.* 52:371-386 (2003); Casu et al., *Plant Mol. Biol.*, 54:503-517 (2004); Casu et al. *Funct. Int. Genomics* 7:153-167 (2007)). Therefore, to fully understand the value of a transgenic promoter for sugar cane biotechnology, promoter activity was assessed over the different developmental stages present within the stem of mature plants. To do this, samples were taken from sugar cane stems at internodes 3 and 4 (immature), internode 8 (maturing), and internode 20 (mature).

A leaf sample equal to approximately four standard hole punches was taken and placed into one well of a 96-well sample block kept on ice. Each plant was sampled in duplicate from the same leaf. Samples were subsequently frozen at −80° C., and freeze-dried prior to analysis. Stem samples were taken, placed on ice, and subsequently frozen at −80° C. Frozen stem was ground to a powder using a standard coffee grinder or similar device, and freeze-dried. Approximately 40 mg of the freeze-dried, powdered stem tissue was placed into one well of a 96-well sample block. Each sample was analyzed in duplicate. GUS expression in the leaf and stem was subsequently quantitated by ELISA.

For the GUS ELISA, high-binding 96-well plates (Nunc Maxisorp) were coated at 4° C. overnight with 2 µg/ml rabbit anti-GUS IgG (Sigma G5545) in 25 mM borate, 75 mM NaCl, pH 8.5 (100 µl/well). Plates were washed three times with 10 mM Tris, pH 8.0 containing 0.05% Tween-20 and 0.2% $NaN_3$. Samples or standards (GUS Type VII-A, Sigma G7646) were added to the plate (100 µl/well), incubated for 1 hr at room temperature with shaking, and washed five times. 100 µl/well of 2 µg/ml horseradish peroxidase (HRP)-labeled rabbit anti-GUS IgG (Invitrogen A5790 conjugated to HRP) was then added to the plate, incubated for 1 hr at room temperature with shaking, and washed as before. The HRP-conjugated antibody was detected by adding 100 µl/well tetramethylbenzidine (TMB, Sigma T0440) and developing for 30 min at room temperature. The reaction was stopped by the addition of 100 µl/well of 0.1N HCl. The absorbance was measured at 450 nm with 620 as a reference using a microplate reader (Tecan Sunrise, Research Triangle Park, N.C.). The GUS standard curve uses a 4-parameter curve fit. The curve is plotted linear vs. log with a range from 0 to 320 ng/ml.

In addition, to assess whether the levels of transgene expression achieved in the T0 plants were maintained in the ratoon, six plants for each construct were selected for further analysis. At maturity (approximately 12 months post transfer to soil), the main stem and any associated tillers of these plants were cut off at the base, and the resulting ratoon plants were analysed after approximately five months (at which time they were roughly equivalent in size to the six-month-old T0 plants). Of the 42 plants that were selected for ratooning, 28 plants successfully ratooned, consisting of between two to five plants for each of the constructs.

Example 4

Gus Expression in the Transformed Sugar Cane Plants

Beta-glucuronidase (GUS) expression in the first unfurled leaf of six-month-old sugar cane plants for each of the constructs is shown in FIG. 1. Constructs having the dual enhancer, eFMVe35S (SEQ ID NO:1) in operative association with the promoter showed significantly enhanced GUS expression as compared to the level of expression of GUS observed for the same construct absent the dual enhancer. Thus, construct SC27 with the dual enhancer and the maize phosphoenolpyruvate carboxylase promoter (PEPC) as compared to construct SC24 with only the PEPC promoter showed an enhancement of protein production of over 6-fold. The results for the maize ubiquitin promoter (ZmUbi) (SC11 v. SC27) showed an enhancement of protein production of over 7-fold.

Figure 2:
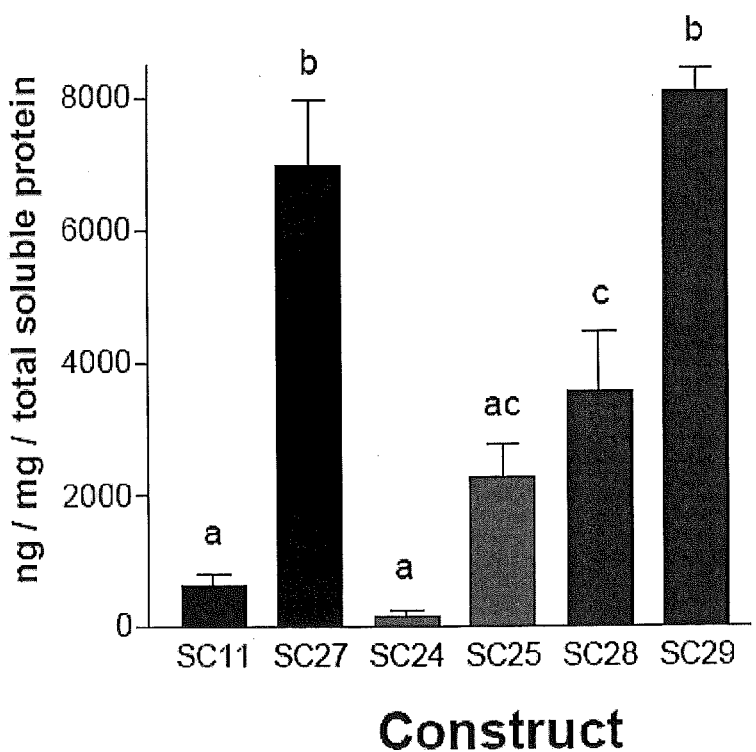
FIG. 2 shows GUS expression by the different promoter-scoGUS constructs in the first unfurled leaf of sugar cane tillers associated with approximately 11-month-old mother plants. SC11 (Zm-Ubi-scoGUS); SC27 (eFMVe35S-ZmUbi-scoGUS); SC24 (ZmPEPC-scoGUS); SC25 (eFMVe35S-ZmPEPC-scoGUS); SC28 (CMP-iUbi-scoGUS); SC29(eFMVe35S-pCMP-iUbi-scoGUS). Shown is the mean (±SEM; n=5). Data with different superscripts are significantly different ($p<0.05$).
Figure 3:
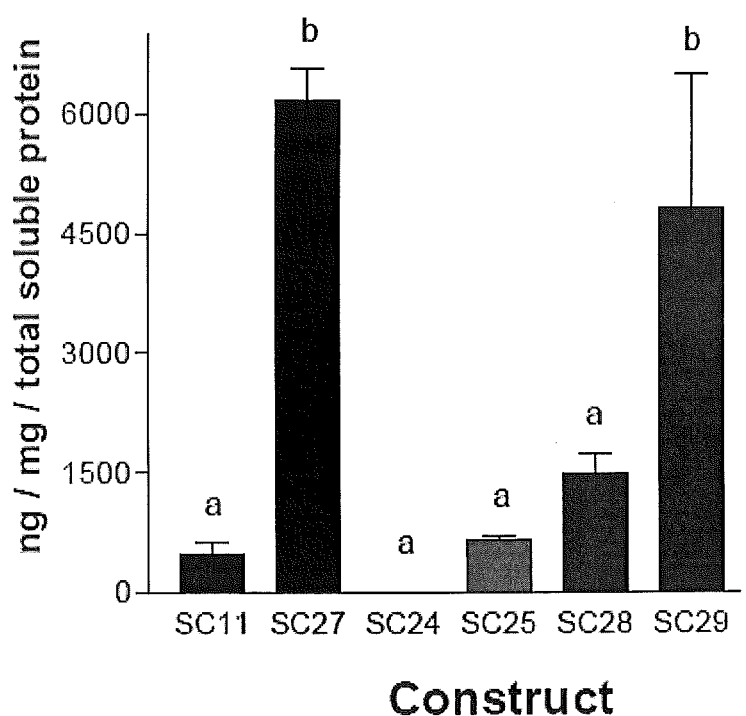
FIG. 3 shows GUS expression by the different promoter-scoGUS constructs in the stem (internodes 3 and 4) of sugar cane tillers associated with approximately 11-month-old mother plants. SC11 (Zm-Ubi1-scoGUS); SC27 (eFMVe35S-ZmUbi-scoGUS); SC24 (ZmPEPC-scoGUS); SC25 (eFMVe35S-ZmPEPC-scoGUS); SC28 (CMP-iUbi-scoGUS); SC29 (eFMVe35S-pCMP-iUbi-scoGUS). Shown is the mean (±SEM; n=5). Data with different superscripts are significantly different ($p<0.05$).

GUS expression in the first unfurled leaf of sugar cane tillers (FIG. 2) and in stems of tillers (FIG. 3) showed similar results to that of the first unfurled leaf of six-month-old sugar cane plants described above (FIG. 1). Overall protein production levels were generally higher in the older plants (whether in the stems (FIG. 2) or leaves (FIG. 3)) but the relative levels of protein production by plants having constructs with the enhancer versus those without the enhancer were significantly higher.

Further evidence of the enhancement of GUS expression by the dual enhancer (eFMVe35S, SEQ ID NO:1) is provided in FIGS. 4A-4B. Specifically, FIG. 4A shows GUS expression in sugar cane stems (immature (internodes 3 and 4), maturing (internode 8), and mature (internode 20)) using the maize ubiquitin promoter (ZmUbi) with and without the enhancer, eFMVe35S. When the enhancer was operatively linked to the ZmUbi promoter, an enhancement of over 7-fold was observed. Expression in the leaves is shown in FIG. 4B where the construct having the enhancer linked to the maize ubiquitin promoter showed a more than 8 fold increase in expression as compared to expression with the promoter alone.

Figure 4:
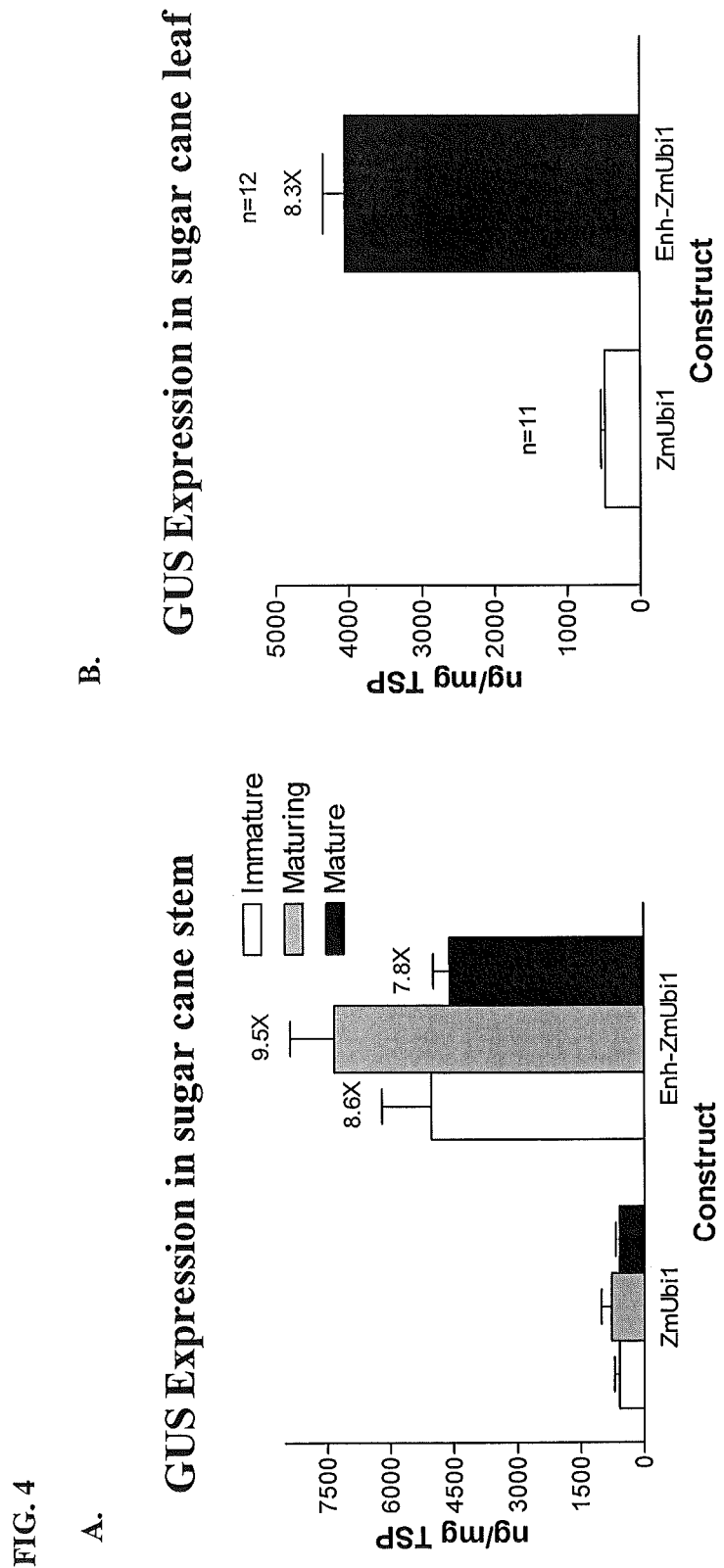
FIGS. 4A-4B show GUS expression by the Zm-Ubi1-scoGUS and eFMVe35S-ZmUbi-scoGUS constructs in sugar cane stems (FIG. 4A) taken from plants at 12 months of age (immature (internodes 3 and 4), maturing (internode 8), and mature (internode 20)) and in the first unfurled leaf of six-month-old sugar cane plants (FIG. 4B). TSP=total soluble protein. Shown is the mean (±SEM.
Figure 5:
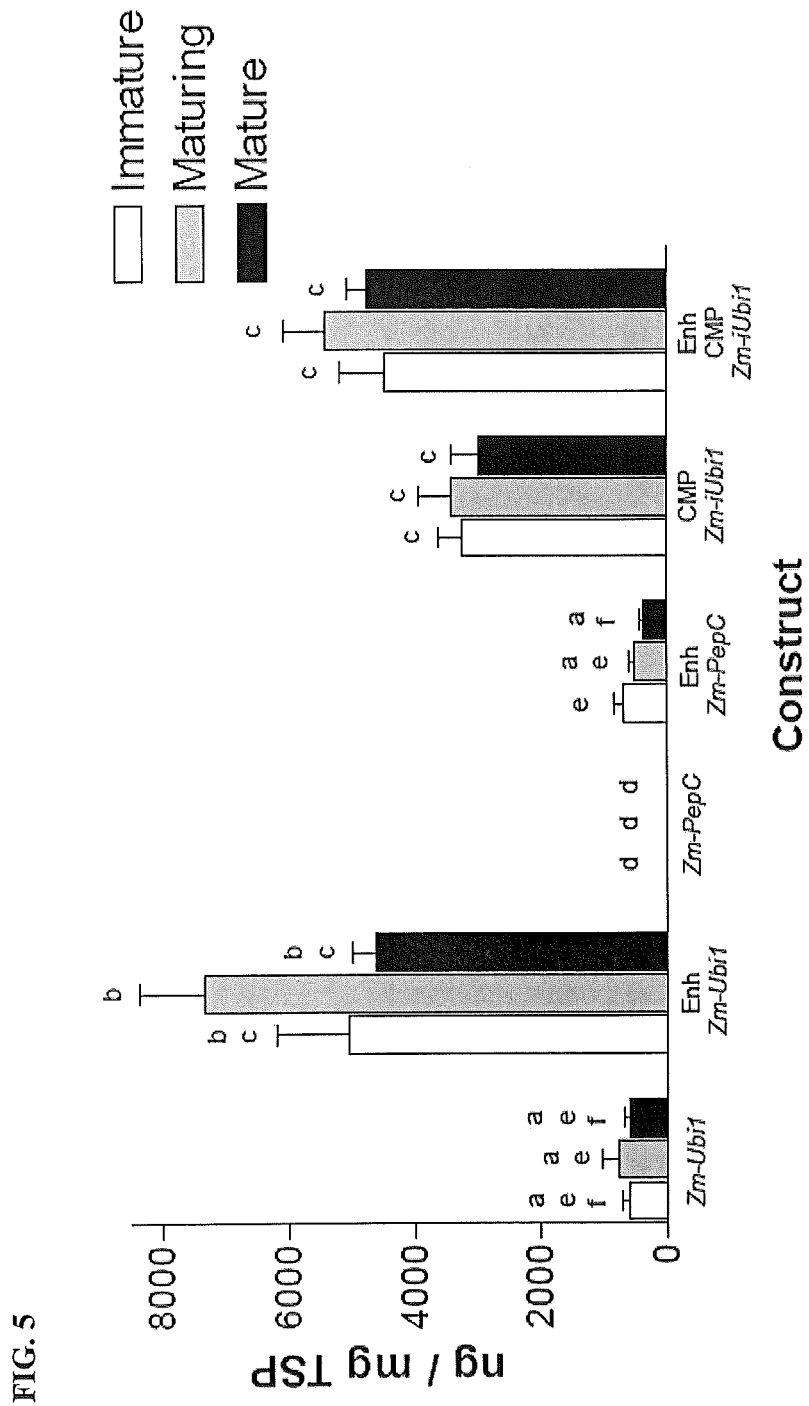
FIG. 5 shows GUS expression in stem of transgenic sugar cane containing the different promoter-scoGUS constructs. Samples were taken from immature (internodes 3&4), maturing (internode 8) and mature (internode 20) stem regions of plants at 12 months post transfer to soil. GUS abundance was measured using qELISA. Shown is the mean (±SEM; n=7). Data with different letters are significantly different (p<0.05).

Similar to FIG. 4, FIG. 5 shows enhancement of GUS expression in the stem of transgenic sugar cane containing each of the different promoter-scoGUS constructs. Samples were taken from immature (internodes 3 and 4), maturing (internode 8) and mature (internode 20) stem regions of plants at 12 months post transfer to soil. Interestingly, the Zm-PEPC promoter which is a leaf preferred promoter, shows expression when operatively associated with the dual enhancer, (eFMVe35S, SEQ ID NO:1). Thus, the dual enhancer appears to alter the leaf preferred expression of the Zm-PEPC promoter, resulting in levels of expression similar to the maize ubiquitin promoter without the enhancer.

Figure 6:
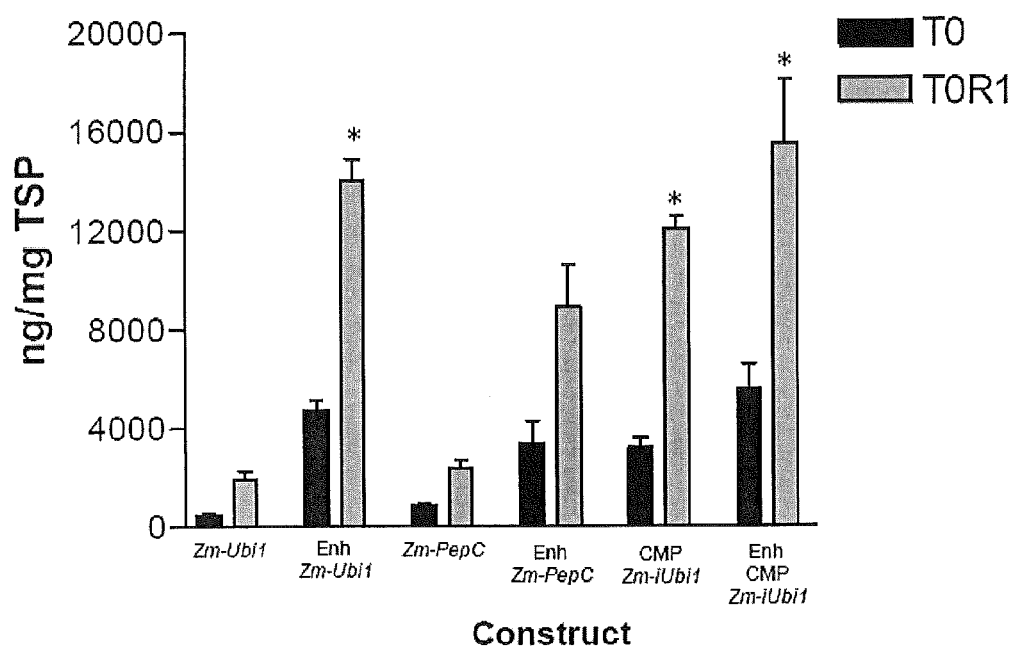
FIG. 6 shows a comparison of GUS expression by the different promoter-scoGUS constructs in the leaf of T0 and ratoon (T0R1) plants. The first, fully unfurled leaf from each independent, transgenic event was analysed at six months post transfer to soil (T0) or five months after ratooning (T0R1; at which time the T0R1 plants were at a comparable height to the six month old T0 plants). GUS abundance was measured using qELISA. Shown is the mean (±SEM or SD (Zm-PepC); n=2-5). * indicates a statistically significant difference relative to the T0 (p<0.001).

Transgene expression in the ratoon was also examined and the results shown in FIG. 6. GUS expression in each of the ratoon plants (T0R1) was higher than the expression observed in the T0 generation, resulting in a substantial increase in the mean expression for each of the constructs. Transgenic T0R1 plants containing the Enh-CMP-Zm-iUbi1 construct showed the highest levels of GUS expression (FIG. 5; mean expression=15.5 ug/mg protein). In addition, one of the Enh-CMP-Zm-iUbi1 events also had the highest overall levels of expression (24.5 ug/mg protein), with GUS levels reaching approximately 2.5% of total soluble leaf protein.

That which is claimed:

1. A sugar cane plant cell comprising a recombinant nucleic acid molecule, the recombinant nucleic acid molecule comprising a nucleotide sequence of interest, a promoter and the nucleotide sequence of SEQ ID NO:1, wherein the promoter is downstream of and in operative association with the nucleotide sequence of SEQ ID NO:1 and upstream of and in operative association with the nucleotide sequence of interest, and the nucleotide sequence of interest is expressed at a level at least about 6 times greater than the level of expression of said nucleotide sequence of interest in a control, further wherein the promoter is a maize polyubiquitin-1 promoter and/or a maize PepC promoter.

2. The sugar cane plant cell of claim 1, wherein the recombinant nucleic acid molecule further comprises a Kozak sequence.

3. A sugar cane plant or sugar cane plant part comprising the plant cell of claim 1.

4. A crop comprising a plurality of the sugar cane plants of claim 3 planted together in an agricultural field.

5. A method of increasing the expression of a nucleotide sequence of interest in a sugar cane plant cell, comprising:
introducing into the sugar cane plant cell a recombinant nucleic acid molecule, the recombinant nucleic acid molecule comprising a nucleotide sequence of interest, a promoter and the nucleotide sequence of SEQ ID NO:1, wherein the promoter is downstream of and in operative association with the nucleotide sequence of SEQ ID NO:1 and upstream of and in operative association with the nucleotide sequence of interest, under conditions where the nucleotide sequence of interest is expressed, further wherein the promoter is a maize polyubiquitin-1 promoter and/or a maize PepC promoter, thereby increasing the level of expression of the nucleotide sequence of interest to at least about 6 times greater than the level of expression of said nucleotide sequence of interest in a control.

6. The method of claim 5, wherein the recombinant nucleic acid molecule further comprises a Kozak sequence.

7. The method of claim 5, further comprising regenerating a plant from the plant cell.

8. A sugar cane plant cell produced by the method of claim 4.

9. A sugar cane plant produced by the method of claim 7.

10. A crop comprising a plurality of the sugar cane plants of claim 9 planted together in an agricultural field.

11. The method of claim 6, further comprising regenerating a plant from the plant cell.

12. A sugar cane plant cell produced by the method of claim 5.

* * * * *

UNITED STATES PATENT AND TRADEMARK OFFICE
CERTIFICATE OF CORRECTION

PATENT NO.         : 9,441,234 B2
APPLICATION NO.    : 14/364184
DATED              : September 13, 2016
INVENTOR(S)        : Kinkema et al.

Page 1 of 1

It is certified that error appears in the above-identified patent and that said Letters Patent is hereby corrected as shown below:

In the Specification

Column 15, Line 43: delete ""co-sequence")," and insert -- "ω-sequence"), --

Column 18, Line 65: delete "as Vip2" and insert -- as *Vip1, Vip2* --

Column 20, Line 6: delete "like; xylanases," and insert -- like; f) xylanases, --

Column 21, Line 6: delete "by" and insert -- bp --

Column 21, Line 8: delete "by" and insert -- bp --

Column 21, Line 20: delete "by" and insert -- bp --

Column 21, Line 22: delete "by" and insert -- bp --

Signed and Sealed this
Ninth Day of May, 2017

Michelle K. Lee
*Director of the United States Patent and Trademark Office*